United States Patent
Liu et al.

(10) Patent No.: US 11,028,393 B2
(45) Date of Patent: *Jun. 8, 2021

(54) SIRNA COMPOSITIONS THAT SPECIFICALLY DOWN REGULATE EXPRESSION OF A VARIANT OF THE PNPLA3 GENE AND METHODS OF USE THEREOF FOR TREATING A CHRONIC LIVER DISEASE

(71) Applicant: Purdue Research Foundation, West Lafayette, IN (US)

(72) Inventors: Wanqing Liu, Zionsville, IN (US); Yoon Yeo, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/735,034

(22) Filed: Jan. 6, 2020

(65) Prior Publication Data

US 2020/0270615 A1 Aug. 27, 2020

Related U.S. Application Data

(63) Continuation of application No. 16/026,609, filed on Jul. 3, 2018, now Pat. No. 10,526,605, which is a continuation of application No. 15/614,147, filed on Jun. 5, 2017, now Pat. No. 10,036,024.

(60) Provisional application No. 62/345,048, filed on Jun. 3, 2016.

(51) Int. Cl.

| C12N 15/11 | (2006.01) |
| C12N 15/113 | (2010.01) |
| A61K 31/713 | (2006.01) |
| A61K 31/7088 | (2006.01) |
| A61K 47/59 | (2017.01) |
| A61K 47/58 | (2017.01) |
| A61K 47/54 | (2017.01) |
| A61K 47/69 | (2017.01) |

(52) U.S. Cl.
CPC ...... *C12N 15/1137* (2013.01); *A61K 31/7088* (2013.01); *A61K 31/713* (2013.01); *A61K 47/554* (2017.08); *A61K 47/58* (2017.08); *A61K 47/59* (2017.08); *A61K 47/6923* (2017.08); *A61K 47/6933* (2017.08); *C12N 2310/14* (2013.01); *C12N 2310/351* (2013.01); *C12N 2320/32* (2013.01); *C12N 2320/34* (2013.01); *C12Y 301/01003* (2013.01)

(58) Field of Classification Search
CPC ............ C12N 15/1137; C12N 2320/32; C12N 2310/351; C12N 2320/34; C12N 2310/14; A61K 31/713; A61K 31/7088; A61K 47/58; A61K 47/6933; A61K 47/554; A61K 47/6923; A61K 47/59; C12Y 301/01003

See application file for complete search history.

(56) References Cited

U.S. PATENT DOCUMENTS

| 4,166,452 A | 9/1979 | Generales, Jr. |
| 4,256,108 A | 3/1981 | Theeuwes |
| 4,265,874 A | 5/1981 | Bonsen et al. |
| 4,683,195 A | 7/1987 | Mullis et al. |
| 4,683,202 A | 7/1987 | Mullis |
| 5,910,488 A | 6/1999 | Nabel et al. |
| 5,962,428 A | 10/1999 | Carrano et al. |
| 5,998,203 A | 12/1999 | Matulic-Adamic et al. |
| 6,573,099 B2 | 6/2003 | Graham |
| 6,753,423 B1 | 6/2004 | Cook et al. |
| 9,273,312 B2 | 3/2016 | Puri et al. |
| 9,289,505 B2 | 3/2016 | Minko et al. |
| 9,289,514 B2 | 3/2016 | Chatterton |
| 9,328,347 B2 | 5/2016 | Stein et al. |
| 9,328,348 B2 | 5/2016 | Zhang et al. |
| 2003/0130186 A1 | 7/2003 | Vargeese et al. |
| 2004/0110296 A1 | 6/2004 | Vargeese et al. |
| 2004/0167090 A1 | 8/2004 | Monahan et al. |
| 2004/0192626 A1 | 9/2004 | McSwiggen et al. |
| 2004/0249178 A1 | 12/2004 | Vargeese et al. |
| 2005/0043219 A1 | 2/2005 | Manoharan et al. |
| 2005/0074771 A1 | 4/2005 | Cook et al. |
| 2005/0107325 A1 | 5/2005 | Manoharan et al. |
| 2005/0119470 A1 | 6/2005 | Manoharan et al. |
| 2005/0153337 A1 | 7/2005 | Manoharan |
| 2005/0158727 A1 | 7/2005 | Manoharan et al. |
| 2005/0239739 A1 | 10/2005 | Matulic-Adamic et al. |
| 2005/0282188 A1 | 12/2005 | Haeberli et al. |
| 2007/0218122 A1 | 9/2007 | MacLachlan et al. |
| 2008/0066206 A1* | 3/2008 | Allen ................ C12N 15/8266 800/298 |
| 2011/0213010 A1* | 9/2011 | Hayden ............... C12Q 1/6883 514/44 A |

FOREIGN PATENT DOCUMENTS

| GB | 2397818 B | 3/2005 |
| WO | WO-2010131907 A2 * | 11/2010 ........... C12N 15/111 |

OTHER PUBLICATIONS

Beaucage et al, "The Funcionalization of Oligonucleotides Via Phosphoramidite Derivatives," Tetrahedron vol. 49, No. 10, 1993, pp. 1925-1963.

Brummelkamp et al, "A system for stable expression of short interfering RNAs in mammalian cells," Science vol. 296, 2002. pp. 550-553.

(Continued)

*Primary Examiner* — Ekaterina Poliakova-Georgantas

(74) *Attorney, Agent, or Firm* — Brown Rudnick LLP; Adam M. Schoen

(57) ABSTRACT

The invention provides siRNA compositions that specifically downregulates expression of a variant of the PNPLA3 gene and methods of use thereof for treating a chronic liver disease or alcoholic liver disease (ALD).

11 Claims, 14 Drawing Sheets

Specification includes a Sequence Listing.

(56) References Cited

OTHER PUBLICATIONS

Buch et al, "A genome-wide association study confirms PNPLA3 and identifies TM6SF2 and MBOAT7 as risk loci for alchol-related cirrhosis," Zurich Open Repository and Archive, 2015, 28 pages.
Calegari et al, "Tissue-specific RNA interference in postimplantation mouse embryos with endoribonuclease-prepared short interfering RNA," Proc. Natl. Acad. Sci. USA vol. 99, No. 22, 2002, pp. 14236-14240.
Donze et al, "RNA interference in mammalian cells using siRNAs synthesized with T7 RNA polymerase," Nucleic Acids Res vol. 30, No. 10, 2002, e46, 4 pages.
Elbashir et al, "RNA interference is mediated by 21- and 22-nucleotide RNAs," Genes Dev 15, 2001, pp. 188-200.
Gubler et al, "A simple and very efficient method for generating cDNA libraries," Gene 25, 1983, pp. 263-269.
Kawasaki et al, "siRNAs generated by recombinant human Dicer induce specific and significant but target site-independent gene silencing in human cells," Nucleic Acids Res, 2003, vol. 31, No. 3, pp. 981-987.
Kiernan et al, "High-Throughput Protein Characterization Using Mass Spectrometric Immunoassay," Anal Biochem, 2002, vol. 301, pp. 49-56.
Knight et al, "A Role for the RNase III Enzyme DCR-1 in RNA Interference and Germ Line Development in Caenorhabditis elegans," Science, Sep. 2001, vol. 293, pp. 2269-2271.
Lee et al, "Expression of small interfering NAs targeted against HIV- rev transcripts in human cells," Nat Biotech, 2002, vol. 19, pp. 500-505.
Lin et al, "A Cytosine Analogue Capable of Clamp-Like Binding to a Guanine in Helical Nucleic Acids," J Am Chem Soc, 1998, vol. 120, pp. 8531-8532.
Loakes, "Survey and Summary The applications of universal DNA base analogues," Nucl Acids Res, 2001, vol. 29, No. 2, pp. 2437-2447.
Mardis, "Next-Generation DNA Sequencing Methods," Annu Rev Genomics Hum Genet 9,, 2008, pp. 387-402.
Mesmaeker et al, "Backbone modifications in oligonucleotides and peptide nucleic acid systems," Stuctural Biologiy, 1995, vol. 4, pp. 343-355.
Miyagishi et al, "U6 promoter-driven siRNAs with four uridine 3' overhangs efficiently suppress targeted gene expression in mamalian cells," Nat Biotech, 2002, vol. 19, pp. 497-500.
Nykanen et al, "ATP Requirements and Small Interfering RNA Structure in the RNA Interference Pathway," Cell, 2001, vol. 107, pp. 309-321.
Paddison et al, "Short haipin RNAs (shRNAs) induce sequence-specific silencing in mammalian cells," Genes Dev, 2002, 16, pp. 948-958.
Parker et al, "mRNA: Detection by In Situ and Northern Hybridization," Methods in Molecular Biology, 1999, vol. 106, 247-283.
Paul et al, "Effective expression of small interfering RNA in human cells," Nat Biotech, 2002, vol. 20, pp. 505-508.
Pingitore et al, "Recombinant PNPLA3 protein shows triglyceride hydrolase activity and its I148M mutation results in loss of function," Biochimica et Biophysica Acta, 204, 1841, pp. 574-580.
Poutanen et al, "Use of matrix-assisted laser desorption/ionization time-of-flight mass mapping and nanospray liquid chromatography/ electrospray ionization tandem mass spectrometry sequence tag analysis for high sensitivity identification of yeast proteins separated by two-dimensional gel electrophoresis," Rapid Commun. Mass Spectrom. 2001, Vo. 15, pp. 1685-1692.
Robertson et al, "Purification and Properties of Ribonuclease III from *Escherichia coli*," J Biol Chem, 1968, vol. 243, No. 1, pp. 82-91.
Scaringe et al, "Chemical synthesis of biologically active oligoriboncleotides using b-cyanoethyl protected ribonucleoside phorphoramidites," Nucl Acids Res, 1990, vol. 18, No. 18, pp. 5433-5441.
Shen, "The rs738409 (I148M) variant of the PNPLA3 gene and cirrhosis: a meta-analysis," Journal of Lipid Research, 2015, vol. 56, pp. 167-175.
Sui et al, "A DNA vector-based RNAi technology to suppress gene expression in mammalian cells," Proc Natl Acad Sci USA, 2002, vol. 99, No. 8, 5515-5520.
Usman et al, "Automated Chemical Synthesis of Long Oligoribonucleotides Using 2'-O-Silylated Ribonucleoside 3'-O-Phosphoramidites on a Controlled-Pore Glass Support: Synthesis of a 43-Nucleotide Sequence Similar o the 3'-Half Molecule of an *Escherichia coli* Formymethionine tRNA1," J Am Chem Soc, 1987, vol. 109, pp. 7845-7854.
Weis et al, "Detection of rare mRNAs via quantitative RT-PCR," Trends in Genetics, 1992, vol. 8, No. 8, pp. 263-264.
Wincott et al, "A Practical Method for the Production of RNA and Ribozymes,"Methods Mol Bio, 1997, vol. 74, pp. 59-68.
Wincott et al, "Synthesis, deprotection, analysis and purification of RNA and ribozymes," Nucl Acids Res, 1995, vol. 23, No. 14, pp. 2677-2684.
Wittrup et al, "Knocking down disease: a progress report on siRNA therapeutics," Nature Reviews / Genetics, 2015, vol. 16 pp. 543-552.
Yang et al, "short RNA duplexes by hydrolysis with *Escherichia coli* RNase III mediate effective RNA interference in mammalian cells," Proc. Natl. Acad. Sci. USA, 2002, vol. 99, No. 15, pp. 9942-9947.
Yu et al, "RNA interference by expression of short-interfering RNAs and hairpin RNA in mammalian cells," Proc Natl Acad Sci USA, 2002, vol. 99, No. 9, pp. 6047-6052.

\* cited by examiner rs738409  rs738408

Chr22-WT – SEQ ID NO.: 553
GCCTTGGTATGTTCCTGCTTCATGCTTCTACAGTGGCCTTATCCCTTCCTTCAGAGGCG

Chr22-Mut – SEQ ID NO.: 554
GCCTTGGTATGTTCCTGCTTCATGCCTTCTACAGTGGCCTTATCCCTTCCTTCAGAGGCG

FIG. 1

SIRNA COMPOSITIONS THAT SPECIFICALLY DOWN REGULATE EXPRESSION OF A VARIANT OF THE PNPLA3 GENE AND METHODS OF USE THEREOF FOR TREATING A CHRONIC LIVER DISEASE

CROSS-REFERENCE TO RELATED APPLICATION

This application is a continuation of U.S. patent application Ser. No. 16/026,609, filed Jul. 3, 2017, which is a continuation of U.S. patent application Ser. No. 15/614,147, filed Jun. 5, 2017, now issued as U.S. Pat. No. 10,036,024, which claims priority to, and the benefit of, U.S. Provisional Patent Application Ser. No. 62/345,048, filed Jun. 3, 2016, the contents of each of which are incorporated by reference.

FIELD OF THE INVENTION

The invention provides siRNA compositions that specifically regulate expression of a variant of the PNPLA3 gene and methods of use thereof for treating a chronic liver disease or alcoholic liver disease (ALD).

BACKGROUND

Nonalcoholic Fatty Liver Disease (NAFLD) is a spectrum of chronic liver disorders, beginning as hepatic fat accumulation without significant alcohol consumption. A subset of patients with NAFLD have nonalcoholic steatohepatitis (NASH) which, over time and without treatment, may progress to cirrhosis and even hepatocellular carcinoma (HCC). It is estimated that 4-22% of HCC cases in the US are due to NASH, and about 2% of the U.S. population has NASH-derived cirrhosis, which is expected to become the leading cause of liver transplantation by 2020. Moreover, NAFLD/NASH is the central hallmark of obesity and type II diabetes which together affect over 50% of the US population, leading to a heavy economic burden. Unfortunately, therapeutic options for NASH are still very limited thus far, with only slight benefits observed from vitamin E or obeticholic acid treatment. Developing safe and effective treatments for NASH remain a significant unmet medical need.

SUMMARY

The invention recognizes that the patatin-like phospholipase domain containing 3 (PNPLA3) gene is strongly associated with chronic human liver disease (e.g., fatty liver disease, steatohepatitis, cirrhosis, alcoholic liver disease and hepatocellular carcinoma). Particularly, the 148 I>M (rs738409 C>G) mutation has been identified as the causal allele for these phenotypes. Overexpression of the 148M isoform is demonstrated herein to be a major cause of these pathogenic processes in both human hepatocytes and animal models. The invention provides small interfering RNA (siRNA) that can specifically recognize the mutant allele (148M) while having minimal effect on the wild-type allele (148I). In that manner, a novel therapeutic strategy for treating human chronic liver disease due to the overexpression of PNPLA3 148M isoform is provided.

In certain aspects, the invention provides compositions that include a small interfering RNA (siRNA) molecule that specifically binds mRNA corresponding to the rs738409 C>G variant of the patatin-like phospholipase domain-containing (PNPLA3) gene, thereby downregulating expression of mutant allele. The rs738409 C>G variant is also referred throughout as the 148M mutant allele or isoform, as opposed to the 148 wild-type allele or isoform. The siRNA molecule may be single stranded or double stranded. In certain embodiments, the siRNA molecule consists of the nucleotide sequence of at least one of SEQ ID NOs 1, 2 or 278-552. In certain embodiments, the siRNA molecule does not bind mRNA associated with the wild-type isoform of the PNPLA3 gene. In other embodiments, the siRNA molecule includes one or more non-naturally occurring nucleotides.

To facilitate effective delivery, the siRNA may be coupled to a pharmaceutically acceptable carrier system. In certain embodiments the pharmaceutically acceptable carrier system includes a nanoparticle to which the siRNA molecule is coupled. An exemplary nanoparticle includes low molecular weight polyethyleneimine (LPEI) or its derivatives (e.g., disulfide crosslinked polyethyleneimine (CLPEI)) and a lipid. In certain embodiments, the lipid is a bile acid, such as cholic acid, deoxycholic acid, and lithocholic acid.

Other aspects of the invention provide methods for treating a subject with a chronic liver disease that involve administrating a therapeutically effective amount of any of the above compositions to a subject having a chronic liver disease. Exemplary chronic liver diseases include fatty liver disease, steatohepatitis, cirrhosis, alcoholic liver disease (ALD), or hepatocellular carcinoma.

Other aspects of the invention provide an allele-specific DNA-based antisense oligo to downregulate expression of the 148M allele.

BRIEF DESCRIPTION OF THE DRAWINGS

FIG. 1 shows the sequence of wild type patatin-like phospholipase domain containing 3 (PNPLA3) gene as well as the sequence of the rs738409 C>G (I148M) variant of the PNPLA3 gene.

DETAILED DESCRIPTION

The invention provides siRNA compositions that specifically downregulate expression of a variant of the PNPLA3 gene and methods of use thereof for treating chronic liver disease. In certain aspects, the invention provides compositions including a small interfering RNA (siRNA) molecule that specifically binds mRNA transcribed from a rs738409 C>G variant of a patatin-like phospholipase domain-containing (PNPLA3) gene.

Figure 5:
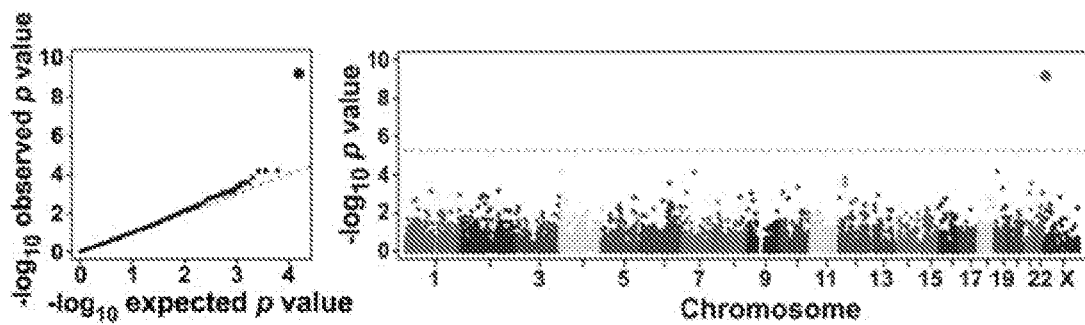
FIG. 5 shows that genetic variation in PNPLA3 confers susceptibility to chronic liver disease.
Figure 6:
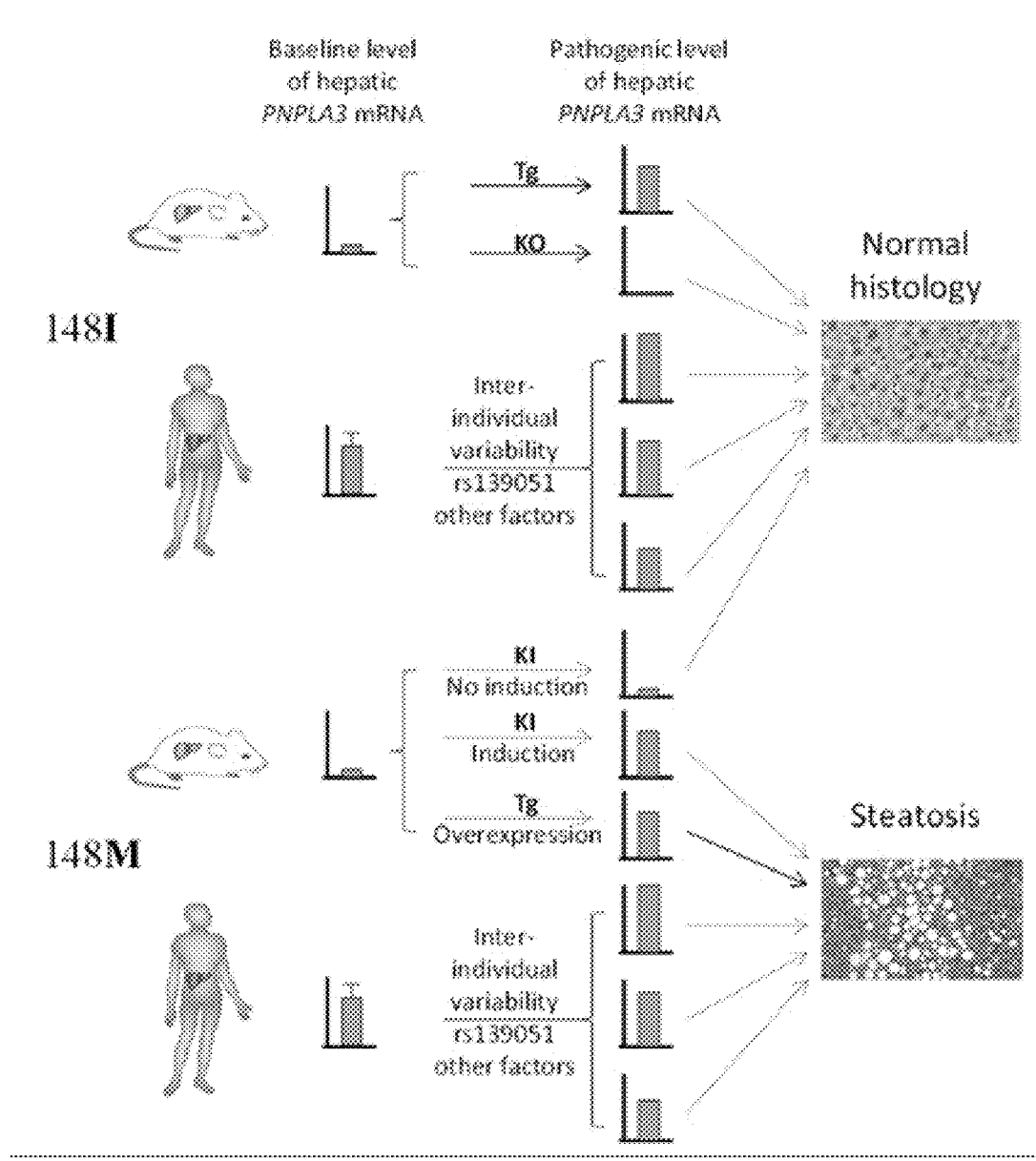
FIG. 6 shows differences between the 148I phenotype and the 148M phenotype.

The patatin-like phospholipase domain-containing (PNPLA3) gene refers to NCBI Gene ID: 80339. FIG. 1 shows the sequence of wild type patatin-like phospholipase domain-containing (PNPLA3) gene as well as the sequence of the rs738409 C>G (I148M) variant of the PNPLA3 gene. Genome-wide association studies (GWAS) in recent years have identified the rs738409 C>G (I148M) variant of the patatin-like phospholipase domain-containing 3 (PNPLA3) gene as the strongest genetic risk allele for NAFLD/NASH, influencing degree of steatosis, grade of inflammation, stage of fibrosis and risk of HCC among all examined populations (FIG. 5). Other studies have also demonstrated the strong association between 148M allele and ALD (Buch et al., (Nature Genetics, 47(12):1443-1447, 2015), the content of which is incorporated by reference herein in its entirety). Notably, NAFLD patients and diabetic patients carrying the 148M mutant allele have over 12- and 19-fold higher risk for the development of HCC, respectively, as compared to those who are 148I carriers, making this mutant allele the single largest genetic risk factor for HCC in the context of NASH. See Liu et al. (Journal of Hepatology, 61:75-81, 2014), the content of which is incorporated by reference herein in its entirety. The 148M allele frequency varies from ~12% among African decedents, 24-40% among Caucasian and East Asian populations to ~50% among Hispanic populations, accounting for a large variability in genetic susceptibility to NAFLD/NASH. Thus far, a number of mechanistic studies have validated the role of the PNPLA3 148M allele in the development of NAFLD. Accordingly, the present invention recognizes that targeting PNPLA3 may provide an ideal therapeutic option for the treatment of NAFLD/NASH. To date, no drug has been developed to target PNPLA3.

While the detailed molecular mechanism underlying the causal role of PNPLA3148M in NAFLD/NASH/ALD still remains incompletely understood, both in vitro cell line studies and in vivo studies using animal models have consistently demonstrated that induction of NAFLD phenotypes requires an "dominant-negative" effect of PNPLA3 (i.e., overexpression of PNPLA3 148M rather than PNPLA3 148I or gene deletion). More specifically, it has been validated that PNPLA3 148M leads to a loss-of-function of its triglycerides hydrolysis activity. However, knockout of the PNPLA3 gene in mice does not lead to NAFLD phenotypes. Overexpression of PNPLA3 148M rather than PNPLA3 148I have been found to induce NAFLD. Moreover, inducing the expression of a PNPLA3 catalytic activity-negative mutant, S47A in a knock-in mouse model parallels the effect of PNPAL3 148M, further highlighting the essential role of the high transcription level of PNPLA3 148M isoform in the development of NAFLD. Given the loss-of-function nature of 148M isoform, conventional therapeutic strategies (e.g., to develop agonist or antagonist chemicals targeting the PNPLA3 protein) are unlikely to block the pathogenic effect of PNPLA3 148M. Instead, specifically reducing the transcription of PNPLA3148M shows great potential.

The invention recognizes that due to its first-pass extract effect, the liver is the organ with the most successful siRNA delivery. Accordingly, the invention provides RNAi-based therapeutics targeting PNPLA3, especially with a capability of allele-specific downregulation of 148M transcription. In certain embodiments, it may be found that the siRNA molecules of the invention are highly specific and potent in downregulating expression of the PNPLA3 148M allele without effecting expression of the PNLPLA3 148I wild-type allele. In certain embodiments, novel nanoparticles capable of siRNA delivery may be used.

The siRNA molecules within the compositions of the invention specifically bind mRNA transcribed from the PNPLA3 148M allele. Here, the term specific or specifically, used in combination with e.g., binding, hybridization, or downregulating refers to binding of a target sequence or downregulation of a target gene's expression with minimal or no binding or downregulation of other nucleic acids or their expression. In particular, mRNA transcribed from the PNPLA3 148I allele (wild-type) is not bound and expression of wild-type PNPLA3 is not downregulated by siRNA of the invention that specifically downregulates expression of the PNPLA3 148M allele. Specific binding as used herein may refer to siRNA that hybridize to a target mRNA sequence under high stringency conditions. Nucleic acid hybridization may be affected by such conditions as salt concentration, temperature, or organic solvents, in addition to base composition, length of complementary strands, and number of nucleotide base mismatches between hybridizing nucleic acids, as is readily appreciated by those skilled in the art. Stringency of hybridization reactions is readily determinable by one of ordinary skill in the art, and generally is an empirical calculation dependent upon sequence length, washing temperature, and salt concentration. In general, longer sequences require higher temperatures for proper annealing, while shorter sequences need lower temperatures. Hybridization generally depends on the ability of denatured DNA to reanneal when complementary strands are present in an environment below its melting temperature. The higher the degree of desired homology between the sequence and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995), the contents of which are incorporated by reference herein in their entirety.

Stringent conditions or high stringency conditions typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 .mu.g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

Moderately stringent conditions may be identified as described by Sambrook et al., Molecular Cloning: A Laboratory Manual, New York: Cold Spring Harbor Press, 1989 (the contents of which are incorporated by reference herein in their entirety), and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37° C. to 50° C. The skilled artisan will recognize how to adjust the temperature, ionic strength, etc. as necessary to accommodate factors such as sequence length and the like.

Interfering RNA (which may be interchangeably referred to as RNAi or an interfering RNA sequence) refers to double-stranded RNA that is capable of silencing, reducing, or inhibiting expression of a target gene by any mechanism of action now known or yet to be disclosed. For example, RNAi may act by mediating the degradation of mRNAs which are complementary to the sequence of the RNAi when the RNAi is in the same cell as the target gene. As used herein, RNAi may refer to double-stranded RNA formed by two complementary RNA strands or by a single, self-complementary strand. RNAi may be substantially or completely complementary to the target mRNA or may comprise one or more mismatches upon alignment to the target mRNA. The sequence of the interfering RNA may correspond to the full length target mRNA, or any subsequence thereof.

The concept of RNAi includes small-interfering RNA, which, herein, may interchangeably be referred to as siRNA. siRNA is described for example in U.S. Pat. Nos. 9,328,347; 9,328,348; 9,289,514; 9,289,505; and 9,273,312, the content of each of which is incorporated by reference herein in its entirety. A siRNA may be any interfering RNA with a duplex length of about 15-60, 15-50, or 15-40 nucleotides in length, more typically about 15-30, 15-25, or 18-23 nucleotides in length. Each complementary sequence of the double-stranded siRNA may be 15-60, 15-50, 15-40, 15-30, 15-25, or 18-23 nucleotides in length, but other noncomplementary sequences may be present. For example, siRNA duplexes may comprise 3' overhangs of 1 to 4 or more nucleotides and/or 5' phosphate termini comprising 1 to 4 or more nucleotides. A siRNA may be synthesized in any of a number of conformations. One skilled in the art would recognize the type of siRNA conformation to be used for a particular purpose. Examples of siRNA conformations include, but need not be limited to, a double-stranded polynucleotide molecule assembled from two separate stranded molecules, wherein one strand is the sense strand and the other is the complementary antisense strand; a double-stranded polynucleotide molecule assembled from a single-stranded molecule, where the sense and antisense regions are linked by a nucleic acid-based or non-nucleic acid-based linker; a double-stranded polynucleotide molecule with a hairpin secondary structure having complementary sense and antisense regions; or a circular single-stranded polynucleotide molecule with two or more loop structures and a stem having self-complementary sense and antisense regions. In the case of the circular polynucleotide, the polynucleotide may be processed either in vivo or in vitro to generate an active double-stranded siRNA molecule.

SiRNA can be chemically synthesized, may be encoded by a plasmid and transcribed, or may be vectored by a virus engineered to express the siRNA. A siRNA may be a single stranded molecule with complementary sequences that self-hybridize into duplexes with hairpin loops. siRNA can also be generated by cleavage of parent dsRNA through the use of an appropriate enzyme such as *E. coli* RNase III or Dicer (Yang et al, Proc. Natl. Acad. Sci. USA 99, 9942-9947 (2002); Calegari et al, Proc. Natl. Acad. Sci. USA 99, 14236-14240 (2002); Byrom et al, Ambion TechNotes 10, 4-6 (2003); Kawasaki et al, Nucleic Acids Res 31, 981-987 (2003); Knight et al, Science 293, 2269-2271 (2001); and Robertson et al, J Biol Chem 243, 82-91 (1968)). A parent dsRNA may be any double stranded RNA duplex from which a siRNA may be produced, such as a full or partial mRNA transcript.

A mismatch motif may be any portion of a siRNA sequence that is not 100% complementary to its target sequence. A siRNA may have zero, one, two, or three or more mismatch regions. The mismatch regions may be contiguous or may be separated by any number of complementary nucleotides. The mismatch motifs or regions may comprise a single nucleotide or may comprise two or more consecutive nucleotides.

A preferred example of a double stranded siRNA design of the invention is listed in Table 1:

TABLE 1

| 1 | 5'-CCUGCUUCAUGCCUUUCUACAGUGG-3' |
|---|---|
| 2 | 3'-AAGGACGAAGUACGGAAAGAUGUCACC-5' |

Exemplary DNA targets for siRNA molecules or antisense oligonucleotides of the invention may include the sequences listed in Table 2 below.

TABLE 2

| SEQ ID NO | DNA target Sequence |
|---|---|
| 3 | GGCCTTGGTATGTTCCTGCTTCATG |
| 4 | GCCTTGGTATGTTCCTGCTTCATG |
| 5 | CCTTGGTATGTTCCTGCTTCATG |
| 6 | CTTGGTATGTTCCTGCTTCATG |
| 7 | TTGGTATGTTCCTGCTTCATG |
| 8 | TGGTATGTTCCTGCTTCATG |
| 9 | GGTATGTTCCTGCTTCATG |
| 10 | GTATGTTCCTGCTTCATG |
| 11 | TATGTTCCTGCTTCATG |
| 12 | ATGTTCCTGCTTCATG |
| 13 | TGTTCCTGCTTCATG |
| 14 | GCCTTGGTATGTTCCTGCTTCATGC |
| 15 | CCTTGGTATGTTCCTGCTTCATGC |

TABLE 2-continued

| SEQ ID NO | DNA target Sequence |
|---|---|
| 16 | CTTGGTATGTTCCTGCTTCATGC |
| 17 | TTGGTATGTTCCTGCTTCATGC |
| 18 | TGGTATGTTCCTGCTTCATGC |
| 19 | GGTATGTTCCTGCTTCATGC |
| 20 | GTATGTTCCTGCTTCATGC |
| 21 | TATGTTCCTGCTTCATGC |
| 22 | ATGTTCCTGCTTCATGC |
| 23 | TGTTCCTGCTTCATGC |
| 24 | GTTCCTGCTTCATGC |
| 25 | CCTTGGTATGTTCCTGCTTCATGCC |
| 26 | CTTGGTATGTTCCTGCTTCATGCC |
| 27 | TTGGTATGTTCCTGCTTCATGCC |
| 28 | TGGTATGTTCCTGCTTCATGCC |
| 29 | GGTATGTTCCTGCTTCATGCC |
| 30 | GTATGTTCCTGCTTCATGCC |
| 31 | TATGTTCCTGCTTCATGCC |
| 32 | ATGTTCCTGCTTCATGCC |
| 33 | TGTTCCTGCTTCATGCC |
| 34 | GTTCCTGCTTCATGCC |
| 35 | TTCCTGCTTCATGCC |
| 36 | CTTGGTATGTTCCTGCTTCATGCCT |
| 37 | TTGGTATGTTCCTGCTTCATGCCT |
| 38 | TGGTATGTTCCTGCTTCATGCCT |
| 39 | GGTATGTTCCTGCTTCATGCCT |
| 40 | GTATGTTCCTGCTTCATGCCT |
| 41 | TATGTTCCTGCTTCATGCCT |
| 42 | ATGTTCCTGCTTCATGCCT |
| 43 | TGTTCCTGCTTCATGCCT |
| 44 | GTTCCTGCTTCATGCCT |
| 45 | TTCCTGCTTCATGCCT |
| 46 | TCCTGCTTCATGCCT |
| 47 | TTGGTATGTTCCTGCTTCATGCCTT |
| 48 | TGGTATGTTCCTGCTTCATGCCTT |
| 49 | GGTATGTTCCTGCTTCATGCCTT |
| 50 | GTATGTTCCTGCTTCATGCCTT |
| 51 | TATGTTCCTGCTTCATGCCTT |
| 52 | ATGTTCCTGCTTCATGCCTT |
| 53 | TGTTCCTGCTTCATGCCTT |
| 54 | GTTCCTGCTTCATGCCTT |
| 55 | TTCCTGCTTCATGCCTT |
| 56 | TCCTGCTTCATGCCTT |
| 57 | CCTGCTTCATGCCTT |
| 58 | TGGTATGTTCCTGCTTCATGCCTTT |
| 59 | GGTATGTTCCTGCTTCATGCCTTT |
| 60 | GTATGTTCCTGCTTCATGCCTTT |
| 61 | TATGTTCCTGCTTCATGCCTTT |
| 62 | ATGTTCCTGCTTCATGCCTTT |
| 63 | TGTTCCTGCTTCATGCCTTT |
| 64 | GTTCCTGCTTCATGCCTTT |
| 65 | TTCCTGCTTCATGCCTTT |
| 66 | TCCTGCTTCATGCCTTT |
| 67 | CCTGCTTCATGCCTTT |
| 68 | CTGCTTCATGCCTTT |
| 69 | GGTATGTTCCTGCTTCATGCCTTTC |
| 70 | GTATGTTCCTGCTTCATGCCTTTC |
| 71 | TATGTTCCTGCTTCATGCCTTTC |
| 72 | ATGTTCCTGCTTCATGCCTTTC |
| 73 | TGTTCCTGCTTCATGCCTTTC |
| 74 | GTTCCTGCTTCATGCCTTTC |
| 75 | TTCCTGCTTCATGCCTTTC |
| 76 | TCCTGCTTCATGCCTTTC |
| 77 | CCTGCTTCATGCCTTTC |
| 78 | CTGCTTCATGCCTTTC |
| 79 | TGCTTCATGCCTTTC |
| 80 | GTATGTTCCTGCTTCATGCCTTTCT |
| 81 | TATGTTCCTGCTTCATGCCTTTCT |
| 82 | ATGTTCCTGCTTCATGCCTTTCT |
| 83 | TGTTCCTGCTTCATGCCTTTCT |
| 84 | GTTCCTGCTTCATGCCTTTCT |
| 85 | TTCCTGCTTCATGCCTTTCT |
| 86 | TCCTGCTTCATGCCTTTCT |
| 87 | CCTGCTTCATGCCTTTCT |
| 88 | CTGCTTCATGCCTTTCT |
| 89 | TGCTTCATGCCTTTCT |
| 90 | GCTTCATGCCTTTCT |
| 91 | TATGTTCCTGCTTCATGCCTTTCTA |
| 92 | ATGTTCCTGCTTCATGCCTTTCTA |
| 93 | TGTTCCTGCTTCATGCCTTTCTA |

TABLE 2-continued

| SEQ ID NO | DNA target Sequence |
|---|---|
| 94 | GTTCCTGCTTCATGCCTTTCTA |
| 95 | TTCCTGCTTCATGCCTTTCTA |
| 96 | TCCTGCTTCATGCCTTTCTA |
| 97 | CCTGCTTCATGCCTTTCTA |
| 98 | CTGCTTCATGCCTTTCTA |
| 99 | TGCTTCATGCCTTTCTA |
| 100 | GCTTCATGCCTTTCTA |
| 101 | CTTCATGCCTTTCTA |
| 102 | ATGTTCCTGCTTCATGCCTTTCTAC |
| 103 | TGTTCCTGCTTCATGCCTTTCTAC |
| 104 | GTTCCTGCTTCATGCCTTTCTAC |
| 105 | TTCCTGCTTCATGCCTTTCTAC |
| 106 | TCCTGCTTCATGCCTTTCTAC |
| 107 | CCTGCTTCATGCCTTTCTAC |
| 108 | CTGCTTCATGCCTTTCTAC |
| 109 | TGCTTCATGCCTTTCTAC |
| 110 | GCTTCATGCCTTTCTAC |
| 111 | CTTCATGCCTTTCTAC |
| 112 | TTCATGCCTTTCTAC |
| 113 | TGTTCCTGCTTCATGCCTTTCTACA |
| 114 | GTTCCTGCTTCATGCCTTTCTACA |
| 115 | TTCCTGCTTCATGCCTTTCTACA |
| 116 | TCCTGCTTCATGCCTTTCTACA |
| 117 | CCTGCTTCATGCCTTTCTACA |
| 118 | CTGCTTCATGCCTTTCTACA |
| 119 | TGCTTCATGCCTTTCTACA |
| 120 | GCTTCATGCCTTTCTACA |
| 121 | CTTCATGCCTTTCTACA |
| 122 | TTCATGCCTTTCTACA |
| 123 | TCATGCCTTTCTACA |
| 124 | GTTCCTGCTTCATGCCTTTCTACAG |
| 125 | TTCCTGCTTCATGCCTTTCTACAG |
| 126 | TCCTGCTTCATGCCTTTCTACAG |
| 127 | CCTGCTTCATGCCTTTCTACAG |
| 128 | CTGCTTCATGCCTTTCTACAG |
| 129 | TGCTTCATGCCTTTCTACAG |
| 130 | GCTTCATGCCTTTCTACAG |
| 131 | CTTCATGCCTTTCTACAG |
| 132 | TTCATGCCTTTCTACAG |
| 133 | TCATGCCTTTCTACAG |
| 134 | CATGCCTTTCTACAG |
| 135 | TTCCTGCTTCATGCCTTTCTACAGT |
| 136 | TCCTGCTTCATGCCTTTCTACAGT |
| 137 | CCTGCTTCATGCCTTTCTACAGT |
| 138 | CTGCTTCATGCCTTTCTACAGT |
| 139 | TGCTTCATGCCTTTCTACAGT |
| 140 | GCTTCATGCCTTTCTACAGT |
| 141 | CTTCATGCCTTTCTACAGT |
| 142 | TTCATGCCTTTCTACAGT |
| 143 | TCATGCCTTTCTACAGT |
| 144 | CATGCCTTTCTACAGT |
| 145 | ATGCCTTTCTACAGT |
| 146 | TCCTGCTTCATGCCTTTCTACAGTG |
| 147 | CCTGCTTCATGCCTTTCTACAGTG |
| 148 | CTGCTTCATGCCTTTCTACAGTG |
| 149 | TGCTTCATGCCTTTCTACAGTG |
| 150 | GCTTCATGCCTTTCTACAGTG |
| 151 | CTTCATGCCTTTCTACAGTG |
| 152 | TTCATGCCTTTCTACAGTG |
| 153 | TCATGCCTTTCTACAGTG |
| 154 | CATGCCTTTCTACAGTG |
| 155 | ATGCCTTTCTACAGTG |
| 156 | TGCCTTTCTACAGTG |
| 157 | CCTGCTTCATGCCTTTCTACAGTGG |
| 158 | CTGCTTCATGCCTTTCTACAGTGG |
| 159 | TGCTTCATGCCTTTCTACAGTGG |
| 160 | GCTTCATGCCTTTCTACAGTGG |
| 161 | CTTCATGCCTTTCTACAGTGG |
| 162 | TTCATGCCTTTCTACAGTGG |
| 163 | TCATGCCTTTCTACAGTGG |
| 164 | CATGCCTTTCTACAGTGG |
| 165 | ATGCCTTTCTACAGTGG |
| 166 | TGCCTTTCTACAGTGG |
| 167 | GCCTTTCTACAGTGG |
| 168 | CTGCTTCATGCCTTTCTACAGTGGC |
| 169 | TGCTTCATGCCTTTCTACAGTGGC |
| 170 | GCTTCATGCCTTTCTACAGTGGC |
| 171 | CTTCATGCCTTTCTACAGTGGC |

TABLE 2-continued

| SEQ ID NO | DNA target Sequence |
|---|---|
| 172 | TTCATGCCTTTCTACAGTGGC |
| 173 | TCATGCCTTTCTACAGTGGC |
| 174 | CATGCCTTTCTACAGTGGC |
| 175 | ATGCCTTTCTACAGTGGC |
| 176 | TGCCTTTCTACAGTGGC |
| 177 | GCCTTTCTACAGTGGC |
| 178 | CCTTTCTACAGTGGC |
| 179 | TGCTTCATGCCTTTCTACAGTGGCC |
| 180 | GCTTCATGCCTTTCTACAGTGGCC |
| 181 | CTTCATGCCTTTCTACAGTGGCC |
| 182 | TTCATGCCTTTCTACAGTGGCC |
| 183 | TCATGCCTTTCTACAGTGGCC |
| 184 | CATGCCTTTCTACAGTGGCC |
| 185 | ATGCCTTTCTACAGTGGCC |
| 186 | TGCCTTTCTACAGTGGCC |
| 187 | GCCTTTCTACAGTGGCC |
| 188 | CCTTTCTACAGTGGCC |
| 189 | CTTTCTACAGTGGCC |
| 190 | GCTTCATGCCTTTCTACAGTGGCCT |
| 191 | CTTCATGCCTTTCTACAGTGGCCT |
| 192 | TTCATGCCTTTCTACAGTGGCCT |
| 193 | TCATGCCTTTCTACAGTGGCCT |
| 194 | CATGCCTTTCTACAGTGGCCT |
| 195 | ATGCCTTTCTACAGTGGCCT |
| 196 | TGCCTTTCTACAGTGGCCT |
| 197 | GCCTTTCTACAGTGGCCT |
| 198 | CCTTTCTACAGTGGCCT |
| 199 | CTTTCTACAGTGGCCT |
| 200 | TTTCTACAGTGGCCT |
| 201 | CTTCATGCCTTTCTACAGTGGCCTT |
| 202 | TTCATGCCTTTCTACAGTGGCCTT |
| 203 | TCATGCCTTTCTACAGTGGCCTT |
| 204 | CATGCCTTTCTACAGTGGCCTT |
| 205 | ATGCCTTTCTACAGTGGCCTT |
| 206 | TGCCTTTCTACAGTGGCCTT |
| 207 | GCCTTTCTACAGTGGCCTT |
| 208 | CCTTTCTACAGTGGCCTT |
| 209 | CTTTCTACAGTGGCCTT |
| 210 | TTTCTACAGTGGCCTT |

TABLE 2-continued

| SEQ ID NO | DNA target Sequence |
|---|---|
| 211 | TTCTACAGTGGCCTT |
| 212 | TTCATGCCTTTCTACAGTGGCCTTA |
| 213 | TCATGCCTTTCTACAGTGGCCTTA |
| 214 | CATGCCTTTCTACAGTGGCCTTA |
| 215 | ATGCCTTTCTACAGTGGCCTTA |
| 216 | TGCCTTTCTACAGTGGCCTTA |
| 217 | GCCTTTCTACAGTGGCCTTA |
| 218 | CCTTTCTACAGTGGCCTTA |
| 219 | CTTTCTACAGTGGCCTTA |
| 220 | TTTCTACAGTGGCCTTA |
| 221 | TTCTACAGTGGCCTTA |
| 222 | TCTACAGTGGCCTTA |
| 223 | TCATGCCTTTCTACAGTGGCCTTAT |
| 224 | CATGCCTTTCTACAGTGGCCTTAT |
| 225 | ATGCCTTTCTACAGTGGCCTTAT |
| 226 | TGCCTTTCTACAGTGGCCTTAT |
| 227 | GCCTTTCTACAGTGGCCTTAT |
| 228 | CCTTTCTACAGTGGCCTTAT |
| 229 | CTTTCTACAGTGGCCTTAT |
| 230 | TTTCTACAGTGGCCTTAT |
| 231 | TTCTACAGTGGCCTTAT |
| 232 | TCTACAGTGGCCTTAT |
| 233 | CTACAGTGGCCTTAT |
| 234 | CATGCCTTTCTACAGTGGCCTTATC |
| 235 | ATGCCTTTCTACAGTGGCCTTATC |
| 236 | TGCCTTTCTACAGTGGCCTTATC |
| 237 | GCCTTTCTACAGTGGCCTTATC |
| 238 | CCTTTCTACAGTGGCCTTATC |
| 239 | CTTTCTACAGTGGCCTTATC |
| 240 | TTTCTACAGTGGCCTTATC |
| 241 | TTCTACAGTGGCCTTATC |
| 242 | TCTACAGTGGCCTTATC |
| 243 | CTACAGTGGCCTTATC |
| 244 | TACAGTGGCCTTATC |
| 245 | ATGCCTTTCTACAGTGGCCTTATCC |
| 246 | TGCCTTTCTACAGTGGCCTTATCC |
| 247 | GCCTTTCTACAGTGGCCTTATCC |
| 248 | CCTTTCTACAGTGGCCTTATCC |
| 249 | CTTTCTACAGTGGCCTTATCC |

TABLE 2-continued

| SEQ ID NO | DNA target Sequence |
|---|---|
| 250 | TTTCTACAGTGGCCTTATCC |
| 251 | TTCTACAGTGGCCTTATCC |
| 252 | TCTACAGTGGCCTTATCC |
| 253 | CTACAGTGGCCTTATCC |
| 254 | TACAGTGGCCTTATCC |
| 255 | ACAGTGGCCTTATCC |
| 256 | TGCCTTTCTACAGTGGCCTTATCCC |
| 257 | GCCTTTCTACAGTGGCCTTATCCC |
| 258 | CCTTTCTACAGTGGCCTTATCCC |
| 259 | CTTTCTACAGTGGCCTTATCCC |
| 260 | TTTCTACAGTGGCCTTATCCC |
| 261 | TTCTACAGTGGCCTTATCCC |
| 262 | TCTACAGTGGCCTTATCCC |
| 263 | CTACAGTGGCCTTATCCC |
| 264 | TACAGTGGCCTTATCCC |
| 265 | TCAGTGGCCTTATCCC |
| 266 | CAGTGGCCTTATCCC |
| 267 | GCCTTTCTACAGTGGCCTTATCCCT |
| 268 | CCTTTCTACAGTGGCCTTATCCCT |
| 269 | CTTTCTACAGTGGCCTTATCCCT |
| 270 | TTTCTACAGTGGCCTTATCCCT |
| 271 | TTCTACAGTGGCCTTATCCCT |
| 272 | TCTACAGTGGCCTTATCCCT |
| 273 | CTACAGTGGCCTTATCCCT |
| 274 | TACAGTGGCCTTATCCCT |
| 275 | ACAGTGGCCTTATCCCT |
| 276 | CAGTGGCCTTATCCCT |
| 277 | AGTGGCCTTATCCCT |

Examples of siRNA molecules targeting mRNAs transcribed from the DNA sequences listed in Table 2 are provided in Table 3 below.

TABLE 3

| SEQ ID NO | siRNA molecule sequence |
|---|---|
| 278 | GGCCUUGGUAUGUUCCUGCUUCAUG |
| 279 | GCCUUGGUAUGUUCCUGCUUCAUG |
| 280 | CCUUGGUAUGUUCCUGCUUCAUG |
| 281 | CUUGGUAUGUUCCUGCUUCAUG |
| 282 | UUGGUAUGUUCCUGCUUCAUG |
| 283 | UGGUAUGUUCCUGCUUCAUG |

TABLE 3-continued

| SEQ ID NO | siRNA molecule sequence |
|---|---|
| 284 | GGUAUGUUCCUGCUUCAUG |
| 285 | GUAUGUUCCUGCUUCAUG |
| 286 | UAUGUUCCUGCUUCAUG |
| 287 | AUGUUCCUGCUUCAUG |
| 288 | UGUUCCUGCUUCAUG |
| 289 | GCCUUGGUAUGUUCCUGCUUCAUGC |
| 290 | CCUUGGUAUGUUCCUGCUUCAUGC |
| 291 | CUUGGUAUGUUCCUGCUUCAUGC |
| 292 | UUGGUAUGUUCCUGCUUCAUGC |
| 293 | UGGUAUGUUCCUGCUUCAUGC |
| 294 | GGUAUGUUCCUGCUUCAUGC |
| 295 | GUAUGUUCCUGCUUCAUGC |
| 296 | UAUGUUCCUGCUUCAUGC |
| 297 | AUGUUCCUGCUUCAUGC |
| 298 | UGUUCCUGCUUCAUGC |
| 299 | GUUCCUGCUUCAUGC |
| 300 | CCUUGGUAUGUUCCUGCUUCAUGCC |
| 301 | CUUGGUAUGUUCCUGCUUCAUGCC |
| 302 | UUGGUAUGUUCCUGCUUCAUGCC |
| 303 | UGGUAUGUUCCUGCUUCAUGCC |
| 304 | GGUAUGUUCCUGCUUCAUGCC |
| 305 | GUAUGUUCCUGCUUCAUGCC |
| 306 | UAUGUUCCUGCUUCAUGCC |
| 307 | AUGUUCCUGCUUCAUGCC |
| 308 | UGUUCCUGCUUCAUGCC |
| 309 | GUUCCUGCUUCAUGCC |
| 310 | UUCCUGCUUCAUGCC |
| 311 | CUUGGUAUGUUCCUGCUUCAUGCCU |
| 312 | UUGGUAUGUUCCUGCUUCAUGCCU |
| 313 | UGGUAUGUUCCUGCUUCAUGCCU |
| 314 | GGUAUGUUCCUGCUUCAUGCCU |
| 315 | GUAUGUUCCUGCUUCAUGCCU |
| 316 | UAUGUUCCUGCUUCAUGCCU |
| 317 | AUGUUCCUGCUUCAUGCCU |
| 318 | UGUUCCUGCUUCAUGCCU |
| 319 | GUUCCUGCUUCAUGCCU |
| 320 | UUCCUGCUUCAUGCCU |
| 321 | UCCUGCUUCAUGCCU |
| 322 | UUGGUAUGUUCCUGCUUCAUGCCUU |

TABLE 3-continued

| SEQ ID NO | siRNA molecule sequence |
|---|---|
| 323 | UGGUAUGUUCCUGCUUCAUGCCUU |
| 324 | GGUAUGUUCCUGCUUCAUGCCUU |
| 325 | GUAUGUUCCUGCUUCAUGCCUU |
| 326 | UAUGUUCCUGCUUCAUGCCUU |
| 327 | AUGUUCCUGCUUCAUGCCUU |
| 328 | UGUUCCUGCUUCAUGCCUU |
| 329 | GUUCCUGCUUCAUGCCUU |
| 330 | UUCCUGCUUCAUGCCUU |
| 331 | UCCUGCUUCAUGCCUU |
| 332 | CCUGCUUCAUGCCUU |
| 333 | UGGUAUGUUCCUGCUUCAUGCCUUU |
| 334 | GGUAUGUUCCUGCUUCAUGCCUUU |
| 335 | GUAUGUUCCUGCUUCAUGCCUUU |
| 336 | UAUGUUCCUGCUUCAUGCCUUU |
| 337 | AUGUUCCUGCUUCAUGCCUUU |
| 338 | UGUUCCUGCUUCAUGCCUUU |
| 339 | GUUCCUGCUUCAUGCCUUU |
| 340 | UUCCUGCUUCAUGCCUUU |
| 341 | UCCUGCUUCAUGCCUUU |
| 342 | CCUGCUUCAUGCCUUU |
| 343 | CUGCUUCAUGCCUUU |
| 344 | GGUAUGUUCCUGCUUCAUGCCUUUC |
| 345 | GUAUGUUCCUGCUUCAUGCCUUUC |
| 346 | UAUGUUCCUGCUUCAUGCCUUUC |
| 347 | AUGUUCCUGCUUCAUGCCUUUC |
| 348 | UGUUCCUGCUUCAUGCCUUUC |
| 349 | GUUCCUGCUUCAUGCCUUUC |
| 350 | UUCCUGCUUCAUGCCUUUC |
| 351 | UCCUGCUUCAUGCCUUUC |
| 352 | CCUGCUUCAUGCCUUUC |
| 353 | CUGCUUCAUGCCUUUC |
| 354 | UGCUUCAUGCCUUUC |
| 355 | GUAUGUUCCUGCUUCAUGCCUUUCU |
| 356 | UAUGUUCCUGCUUCAUGCCUUUCU |
| 357 | AUGUUCCUGCUUCAUGCCUUUCU |
| 358 | UGUUCCUGCUUCAUGCCUUUCU |
| 359 | GUUCCUGCUUCAUGCCUUUCU |
| 360 | UUCCUGCUUCAUGCCUUUCU |
| 361 | UCCUGCUUCAUGCCUUUCU |
| 362 | CCUGCUUCAUGCCUUUCU |
| 363 | CUGCUUCAUGCCUUUCU |
| 364 | UGCUUCAUGCCUUUCU |
| 365 | GCUUCAUGCCUUUCU |
| 366 | UAUGUUCCUGCUUCAUGCCUUUCUA |
| 367 | AUGUUCCUGCUUCAUGCCUUUCUA |
| 368 | UGUUCCUGCUUCAUGCCUUUCUA |
| 369 | GUUCCUGCUUCAUGCCUUUCUA |
| 370 | UUCCUGCUUCAUGCCUUUCUA |
| 371 | UCCUGCUUCAUGCCUUUCUA |
| 372 | CCUGCUUCAUGCCUUUCUA |
| 373 | CUGCUUCAUGCCUUUCUA |
| 374 | UGCUUCAUGCCUUUCUA |
| 375 | GCUUCAUGCCUUUCUA |
| 376 | CUUCAUGCCUUUCUA |
| 377 | AUGUUCCUGCUUCAUGCCUUUCUAC |
| 378 | UGUUCCUGCUUCAUGCCUUUCUAC |
| 379 | GUUCCUGCUUCAUGCCUUUCUAC |
| 380 | UUCCUGCUUCAUGCCUUUCUAC |
| 381 | UCCUGCUUCAUGCCUUUCUAC |
| 382 | CCUGCUUCAUGCCUUUCUAC |
| 383 | CUGCUUCAUGCCUUUCUAC |
| 384 | UGCUUCAUGCCUUUCUAC |
| 385 | GCUUCAUGCCUUUCUAC |
| 386 | CUUCAUGCCUUUCUAC |
| 387 | UUCAUGCCUUUCUAC |
| 388 | UGUUCCUGCUUCAUGCCUUUCUACA |
| 389 | GUUCCUGCUUCAUGCCUUUCUACA |
| 390 | UUCCUGCUUCAUGCCUUUCUACA |
| 391 | UCCUGCUUCAUGCCUUUCUACA |
| 392 | CCUGCUUCAUGCCUUUCUACA |
| 393 | CUGCUUCAUGCCUUUCUACA |
| 394 | UGCUUCAUGCCUUUCUACA |
| 395 | GCUUCAUGCCUUUCUACA |
| 396 | CUUCAUGCCUUUCUACA |
| 397 | UUCAUGCCUUUCUACA |
| 398 | UCAUGCCUUUCUACA |
| 399 | GUUCCUGCUUCAUGCCUUUCUACAG |
| 400 | UUCCUGCUUCAUGCCUUUCUACAG |

TABLE 3-continued

| SEQ ID NO | siRNA molecule sequence |
|---|---|
| 401 | UCCUGCUUCAUGCCUUUCUACAG |
| 402 | CCUGCUUCAUGCCUUUCUACAG |
| 403 | CUGCUUCAUGCCUUUCUACAG |
| 404 | UGCUUCAUGCCUUUCUACAG |
| 405 | GCUUCAUGCCUUUCUACAG |
| 406 | CUUCAUGCCUUUCUACAG |
| 407 | UUCAUGCCUUUCUACAG |
| 408 | UCAUGCCUUUCUACAG |
| 409 | CAUGCCUUUCUACAG |
| 410 | UUCCUGCUUCAUGCCUUUCUACAGU |
| 411 | UCCUGCUUCAUGCCUUUCUACAGU |
| 412 | CCUGCUUCAUGCCUUUCUACAGU |
| 413 | CUGCUUCAUGCCUUUCUACAGU |
| 414 | UGCUUCAUGCCUUUCUACAGU |
| 415 | GCUUCAUGCCUUUCUACAGU |
| 416 | CUUCAUGCCUUUCUACAGU |
| 417 | UUCAUGCCUUUCUACAGU |
| 418 | UCAUGCCUUUCUACAGU |
| 419 | CAUGCCUUUCUACAGU |
| 420 | AUGCCUUUCUACAGU |
| 421 | UCCUGCUUCAUGCCUUUCUACAGUG |
| 422 | CCUGCUUCAUGCCUUUCUACAGUG |
| 423 | CUGCUUCAUGCCUUUCUACAGUG |
| 424 | UGCUUCAUGCCUUUCUACAGUG |
| 425 | GCUUCAUGCCUUUCUACAGUG |
| 426 | CUUCAUGCCUUUCUACAGUG |
| 427 | UUCAUGCCUUUCUACAGUG |
| 428 | UCAUGCCUUUCUACAGUG |
| 429 | CAUGCCUUUCUACAGUG |
| 430 | AUGCCUUUCUACAGUG |
| 431 | UGCCUUUCUACAGUG |
| 432 | CCUGCUUCAUGCCUUUCUACAGUGG |
| 433 | CUGCUUCAUGCCUUUCUACAGUGG |
| 434 | UGCUUCAUGCCUUUCUACAGUGG |
| 435 | GCUUCAUGCCUUUCUACAGUGG |
| 436 | CUUCAUGCCUUUCUACAGUGG |
| 437 | UUCAUGCCUUUCUACAGUGG |
| 438 | UCAUGCCUUUCUACAGUGG |
| 439 | CAUGCCUUUCUACAGUGG |
| 440 | AUGCCUUUCUACAGUGG |
| 441 | UGCCUUUCUACAGUGG |
| 442 | GCCUUUCUACAGUGG |
| 443 | CUGCUUCAUGCCUUUCUACAGUGGC |
| 444 | UGCUUCAUGCCUUUCUACAGUGGC |
| 445 | GCUUCAUGCCUUUCUACAGUGGC |
| 446 | CUUCAUGCCUUUCUACAGUGGC |
| 447 | UUCAUGCCUUUCUACAGUGGC |
| 448 | UCAUGCCUUUCUACAGUGGC |
| 449 | CAUGCCUUUCUACAGUGGC |
| 450 | AUGCCUUUCUACAGUGGC |
| 451 | UGCCUUUCUACAGUGGC |
| 452 | GCCUUUCUACAGUGGC |
| 453 | CCUUUCUACAGUGGC |
| 454 | UGCUUCAUGCCUUUCUACAGUGGCC |
| 455 | GCUUCAUGCCUUUCUACAGUGGCC |
| 456 | CUUCAUGCCUUUCUACAGUGGCC |
| 457 | UUCAUGCCUUUCUACAGUGGCC |
| 458 | UCAUGCCUUUCUACAGUGGCC |
| 459 | CAUGCCUUUCUACAGUGGCC |
| 460 | AUGCCUUUCUACAGUGGCC |
| 461 | UGCCUUUCUACAGUGGCC |
| 462 | GCCUUUCUACAGUGGCC |
| 463 | CCUUUCUACAGUGGCC |
| 464 | CUUUCUACAGUGGCC |
| 465 | GCUUCAUGCCUUUCUACAGUGGCCU |
| 466 | CUUCAUGCCUUUCUACAGUGGCCU |
| 467 | UUCAUGCCUUUCUACAGUGGCCU |
| 468 | UCAUGCCUUUCUACAGUGGCCU |
| 469 | CAUGCCUUUCUACAGUGGCCU |
| 470 | AUGCCUUUCUACAGUGGCCU |
| 471 | UGCCUUUCUACAGUGGCCU |
| 472 | GCCUUUCUACAGUGGCCU |
| 473 | CCUUUCUACAGUGGCCU |
| 474 | CUUUCUACAGUGGCCU |
| 475 | UUUCUACAGUGGCCU |
| 476 | CUUCAUGCCUUUCUACAGUGGCCUU |
| 477 | UUCAUGCCUUUCUACAGUGGCCUU |
| 478 | UCAUGCCUUUCUACAGUGGCCUU |

TABLE 3-continued

| SEQ ID NO | siRNA molecule sequence |
| --- | --- |
| 479 | CAUGCCUUUCUACAGUGGCCUU |
| 480 | AUGCCUUUCUACAGUGGCCUU |
| 481 | UGCCUUUCUACAGUGGCCUU |
| 482 | GCCUUUCUACAGUGGCCUU |
| 483 | CCUUUCUACAGUGGCCUU |
| 484 | CUUUCUACAGUGGCCUU |
| 485 | UUUCUACAGUGGCCUU |
| 486 | UUCUACAGUGGCCUU |
| 487 | UUCAUGCCUUUCUACAGUGGCCUUA |
| 488 | UCAUGCCUUUCUACAGUGGCCUUA |
| 489 | CAUGCCUUUCUACAGUGGCCUUA |
| 490 | AUGCCUUUCUACAGUGGCCUUA |
| 491 | UGCCUUUCUACAGUGGCCUUA |
| 492 | GCCUUUCUACAGUGGCCUUA |
| 493 | CCUUUCUACAGUGGCCUUA |
| 494 | CUUUCUACAGUGGCCUUA |
| 495 | UUUCUACAGUGGCCUUA |
| 496 | UUCUACAGUGGCCUUA |
| 497 | UCUACAGUGGCCUUA |
| 498 | UCAUGCCUUUCUACAGUGGCCUUAU |
| 499 | CAUGCCUUUCUACAGUGGCCUUAU |
| 500 | AUGCCUUUCUACAGUGGCCUUAU |
| 501 | UGCCUUUCUACAGUGGCCUUAU |
| 502 | GCCUUUCUACAGUGGCCUUAU |
| 503 | CCUUUCUACAGUGGCCUUAU |
| 504 | CUUUCUACAGUGGCCUUAU |
| 505 | UUUCUACAGUGGCCUUAU |
| 506 | UUCUACAGUGGCCUUAU |
| 507 | UCUACAGUGGCCUUAU |
| 508 | CUACAGUGGCCUUAU |
| 509 | CAUGCCUUUCUACAGUGGCCUUAUC |
| 510 | AUGCCUUUCUACAGUGGCCUUAUC |
| 511 | UGCCUUUCUACAGUGGCCUUAUC |
| 512 | GCCUUUCUACAGUGGCCUUAUC |
| 513 | CCUUUCUACAGUGGCCUUAUC |
| 514 | CUUUCUACAGUGGCCUUAUC |
| 515 | UUUCUACAGUGGCCUUAUC |
| 516 | UUCUACAGUGGCCUUAUC |
| 517 | UCUACAGUGGCCUUAUC |
| 518 | CUACAGUGGCCUUAUC |
| 519 | UACAGUGGCCUUAUC |
| 520 | AUGCCUUUCUACAGUGGCCUUAUCC |
| 521 | UGCCUUUCUACAGUGGCCUUAUCC |
| 522 | GCCUUUCUACAGUGGCCUUAUCC |
| 523 | CCUUUCUACAGUGGCCUUAUCC |
| 524 | CUUUCUACAGUGGCCUUAUCC |
| 525 | UUUCUACAGUGGCCUUAUCC |
| 526 | UUCUACAGUGGCCUUAUCC |
| 527 | UCUACAGUGGCCUUAUCC |
| 528 | CUACAGUGGCCUUAUCC |
| 529 | UACAGUGGCCUUAUCC |
| 530 | ACAGUGGCCUUAUCC |
| 531 | UGCCUUUCUACAGUGGCCUUAUCCC |
| 532 | GCCUUUCUACAGUGGCCUUAUCCC |
| 533 | CCUUUCUACAGUGGCCUUAUCCC |
| 534 | CUUUCUACAGUGGCCUUAUCCC |
| 535 | UUUCUACAGUGGCCUUAUCCC |
| 536 | UUCUACAGUGGCCUUAUCCC |
| 537 | UCUACAGUGGCCUUAUCCC |
| 538 | CUACAGUGGCCUUAUCCC |
| 539 | UACAGUGGCCUUAUCCC |
| 540 | UCAGUGGCCUUAUCCC |
| 541 | CAGUGGCCUUAUCCC |
| 542 | GCCUUUCUACAGUGGCCUUAUCCCU |
| 543 | CCUUUCUACAGUGGCCUUAUCCCU |
| 544 | CUUUCUACAGUGGCCUUAUCCCU |
| 545 | UUUCUACAGUGGCCUUAUCCCU |
| 546 | UUCUACAGUGGCCUUAUCCCU |
| 547 | UCUACAGUGGCCUUAUCCCU |
| 548 | CUACAGUGGCCUUAUCCCU |
| 549 | UACAGUGGCCUUAUCCCU |
| 550 | ACAGUGGCCUUAUCCCU |
| 551 | CAGUGGCCUUAUCCCU |
| 552 | AGUGGCCUUAUCCCU |

A siRNA molecule may be capable of inhibiting the expression of a target gene, such as the PNPLA3 148M allele. Herein, the terms "silencing" or "reducing" may be used interchangeably with "inhibiting." To examine the extent of inhibition of expression by a siRNA, a siRNA of interest may be added to a test sample and monitored for expression along with a negative control sample to which the siRNA was not added. Preferably, a negative control sample will be similar to the test sample. More preferably, the negative control sample will be identical to the test sample. Examples of negative control samples include untreated samples, samples to which a siRNA-free buffer was added, or samples to which a negative control or mock siRNA was added. Expression in the test sample can then be compared to expression in the negative control sample. Expression may be measured by the detection of any expression product known in the art or yet to be disclosed. Typical expression products that may be detected include RNA and protein.

Methods known in the art for the detection and quantification of RNA expression in a sample include northern blotting and in situ hybridization (Parker and Barnes, Methods in Molecular Biology 106, 247-283 (1999) incorporated by reference herein in its entirety); RNAse protection assays (Hod, Biotechniques 13, 852-854 (1992) incorporated by reference herein in its entirety); and PCR-based methods, such as reverse transcription polymerase chain reaction (RT-PCR) (Weis et al., Trends in Genetics 8, 263-264 (1992) incorporated by reference herein in its entirety). Representative methods for sequencing-based gene expression analysis include Serial Analysis of Gene Expression (SAGE), and gene expression analysis by massively parallel signature sequencing (MPSS). (See Mardis E R, Annu Rev Genomics Hum Genet 9, 387-402 (2008))(the content of which is incorporated by reference herein in its entirety).

Proteins, for example, can be detected and quantified through epitopes recognized by polyclonal and/or monoclonal antibodies used in methods such as ELISA, immunoblot assays, flow cytometric assays, immunohistochemical assays, radioimmuno assays, Western blot assays, an immunofluorescent assays, chemiluminescent assays and other polypeptide detection strategies. Proteins may also be detected by mass spectrometry assays (potentially coupled to immunoaffinity assays) including matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS). Additionally, protein expression may be detected by tagging of proteins separated by two-dimensional polyacrylamide gel electrophoresis (2D-PAGE), (Kiernan et al, Anal Biochem 301, 49-56 (2002); Poutanen et al, Mass Spectrom 15, 1685-1692 (2001) the content of each of which is incorporated by reference herein in its entirety) or any other method of detecting protein.

In general, negative control samples are assigned a value of 100%. Inhibition of expression of a target gene may be achieved when the expression of the test sample relative to the control sample is 95%, 90%, 85%, 80%, 75%, 70%, 65%, 60%, 55%, 50%, 45%, 40%, 35%, 30%, 25%, 20%, 15%, 10%, 5%, 1%, less than 1% or 0%. Expression of a test sample relative to a negative control sample may also be presented in terms of fold reduction, such as a 2-fold, 3-fold, 5-fold, 10-fold, 20-fold, 50-fold, or 100-fold less expression than the negative control sample.

Two or more nucleic acid sequences or subsequences may be referred to as being substantially identical, meaning that they are exactly the same or have a specified percentage of nucleotides that are the same. Substantially identical nucleotides may have at least 60%, 65%, 70%, 75%, 80%, 85%, 90%, 95%, or more than 95% identity over a specified region when compared and aligned for maximum correspondence. This definition, when the context indicates, also refers to the complement of a sequence. Preferably, the substantial identity exists over a region that is at least about 5, 10, 15, 20, 25, 30, 35, 40, 45, 50, 55, or 60 nucleotides in length.

SiRNA molecules can be provided in several forms including, e.g., as one or more isolated siRNA duplexes, as longer double-stranded RNA (dsRNA), or as siRNA or dsRNA transcribed from a transcriptional cassette in a DNA plasmid. The siRNA sequences may have overhangs (as 3' or 5' overhangs as described in Elbashir et al, Genes Dev 15, 188 (2001) or Nykanen et al, Cell 107, 309 (2001), the content of each of which is incorporated by reference herein in its entirety) or may lack overhangs (i.e., have blunt ends).

One or more DNA plasmids encoding one or more siRNA templates may be used to provide siRNA. siRNA can be transcribed as sequences that automatically fold into duplexes with hairpin loops from DNA templates in plasmids having RNA polymerase Ill transcriptional units, for example, based on the naturally occurring transcription units for small nuclear RNA U6 or human RNase P RNA H1 (Brummelkamp et al, Science 296, 550 (2002); Donze et al, Nucleic Acids Res 30, e46 (2002); Paddison et al, Genes Dev 16, 948 (2002); Yu et al, Proc Natl Acad Sci USA 99, 6047 (2002); Lee et al, Nat Biotech, 20, 500 (2002); Miyagishi et al, Nat Biotech 20, 497 (2002); Paul et al, Nat Biotech, 20, 505 (2002); and Sui et al, Proc Natl Acad Sci USA, 99, 5515 (2002); the content of each of which is incorporated by reference herein in its entirety). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp et al (2002) supra). The selected promoter can provide for constitutive or inducible transcription. Compositions and methods for DNA-directed transcription of RNA interference molecules are described in detail in U.S. Pat. No. 6,573,099, incorporated by reference herein in its entirety. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488, the content of each of which is incorporated by reference herein in its entirety. The selected plasmid can provide for transient or stable delivery of a nucleic acid to a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler and Hoffman, Gene 25, 263-269 (1983); Sambrook and Russell, Molecular Cloning: A Laboratory Manual, Cold Spring Harbor Laboratory Press, Cold Spring Harbor N.Y., (2001), the content of each of which is incorporated by reference herein in its entirety) as are PCR methods (see, U.S. Pat. Nos. 4,683,195 and 4,683,202; PCR Protocols: A Guide to Methods and Applications, Innis et al, eds, (1990), the content of each of which is incorporated by reference herein in its entirety). Expression libraries are also well known to those of skill in the art. Additional basic texts disclosing the general methods of use in this invention include Sambrook and Russell (2001) supra; Kriegler, Gene Transfer and Expression: A Laboratory Manual (1990); and Current Protocols in Molecular Biology (Ausubel et al., eds., 1994), the content of each of which is incorporated by reference herein in its entirety.

A siRNA molecule may be chemically synthesized. In one example of chemical synthesis, a single-stranded nucleic acid that includes the siRNA duplex sequence can be synthesized using any of a variety of techniques known in the art, such as those described in Usman et al, J Am Chem Soc, 109, 7845 (1987); Scaringe et al, Nucl Acids Res, 18, 5433 (1990); Wincott et al, Nucl Acids Res, 23, 2677-2684 (1995); and Wincott et al, Methods Mol Bio 74, 59 (1997), the content of each of which is incorporated by reference herein in its entirety. Synthesis of the single-stranded nucleic acid makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer (Thermo Fisher Scientific, Waltham, Mass.) using a 0.2 micromolar scale protocol with a 2.5 min coupling step for 2'-O-methylated nucleotides. Alternatively, syntheses at the 0.2 micromolar scale can be performed on a 96-well plate synthesizer from Thermo Fisher Scientific. However, larger or smaller scale synthesis are also encompassed by the invention, including any method of synthesis now known or yet to be disclosed. Suitable reagents for synthesis of siRNA single-stranded molecules, methods for RNA deprotection, and methods for RNA purification are known to those of skill in the art.

In certain embodiments, siRNA can be synthesized via a tandem synthesis technique, wherein both strands are synthesized as a single continuous fragment or strand separated by a linker that is subsequently cleaved to provide separate fragments or strands that hybridize to form a siRNA duplex. Linkers may be any linker, including a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. In some embodiments, siRNA can be assembled from two distinct single-stranded molecules, wherein one strand includes the sense strand and the other includes the antisense strand of the siRNA. For example, each strand can be synthesized separately and joined together by hybridization or ligation following synthesis and/or deprotection. Either the sense or the antisense strand may contain additional nucleotides that are not complementary to one another and do not form a double stranded siRNA. In certain instances, siRNA molecules can be synthesized as a single continuous fragment, where the self-complementary sense and antisense regions hybridize to form a siRNA duplex having hairpin secondary structure.

A siRNA molecule may comprise a duplex having two complementary strands that form a double-stranded region with least one modified nucleotide in the double-stranded region. The modified nucleotide may be on one strand or both. If the modified nucleotide is present on both strands, it may be in the same or different positions on each strand. A modified siRNA may be less immunostimulatory than a corresponding unmodified siRNA sequence, but retains the capability of silencing the expression of a target sequence.

Examples of modified nucleotides suitable for use in the present invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a conformation such as those described in the art, for example in Saenger, Principles of Nucleic Acid Structure, Springer-Verlag Ed. (1984), incorporated by reference herein in its entirety, are also suitable for use in siRNA molecules. Other modified nucleotides include, without limitation: locked nucleic acid (LNA) nucleotides, G-clamp nucleotides, or nucleotide base analogs. LNA nucleotides include but need not be limited to 2'-O, 4'-C-methylene-(D-ribofuranosyl)nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2Cl) nucleotides, and 2'-azido nucleotides. A G-clamp nucleotide refers to a modified cytosine analog wherein the modifications confer the ability to hydrogen bond both Watson-Crick and Hoogsteen faces of a complementary guanine nucleotide within a duplex (Lin et al, J Am Chem Soc, 120, 8531-8532 (1998) incorporated by reference herein in its entirety). Nucleotide base analogs include for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (Loakes, Nucl Acids Res, 29, 2437-2447 (2001) incorporated by reference herein in its entirety).

A siRNA molecule may comprise one or more chemical modifications such as terminal cap moieties, phosphate backbone modifications, and the like. Examples of classes of terminal cap moieties include, without limitation, inverted deoxy abasic residues, glyceryl modifications, 4',5'-methylene nucleotides, 1-(.beta.-D-erythrofuranosyl) nucleotides, 4'-thio nucleotides, carbocyclic nucleotides, 1,5-anhydrohexitol nucleotides, L-nucleotides, .alpha.-nucleotides, modified base nucleotides, threo pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-aminoalkyl phosphate, 1,3-diamino-2-propyl phosphate, 3 aminopropyl phosphate, 6-aminohexyl phosphate, 1,2-aminododecyl phosphate, hydroxypropyl phosphate, 1,4-butanediol phosphate, 3'-phosphoramidate, 5' phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al, Tetrahedron 49, 1925 (1993); the content of each of which is incorporated by reference herein in its entirety). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al, Modern Synthetic Methods, VCH, 331-417 (1995); Mesmaeker et al, Antisense Research, ACS, 24-39 (1994); the content of each of which is incorporated by reference herein in its entirety). Such chemical modifications can occur at the 5'-end and/or 3'-end of the sense strand, antisense strand, or both strands of the siRNA.

The sense and/or antisense strand of a siRNA may comprise a 3'-terminal overhang having 1 to 4 or more 2'-deoxyribonucleotides and/or any combination of modified and unmodified nucleotides. Additional examples of modified nucleotides and types of chemical modifications that can be introduced into the modified siRNA molecules of the present invention are described, e.g., in UK Patent No. GB 2,397, 818 B and U.S. Patent Publication Nos. 20040192626 and 20050282188, the content of each of which is incorporated by reference herein in its entirety.

A siRNA molecule may comprise one or more non-nucleotides in one or both strands of the siRNA. A non-nucleotide may be any subunit, functional group, or other molecular entity capable of being incorporated into a nucleic acid chain in the place of one or more nucleotide units that is not or does not comprise a commonly recognized nucleotide base such as adenosine, guanine, cytosine, uracil, or thymine, such as a sugar or phosphate.

Chemical modification of siRNA may comprise attaching a conjugate to a siRNA molecule. The conjugate can be attached at the 5'- and/or the 3'-end of the sense and/or the antisense strand of the siRNA via a covalent attachment such as a nucleic acid or non-nucleic acid linker. The conjugate can be attached to the siRNA through a carbamate group or other linking group (see, e.g., U.S. Patent Publication Nos. 20050074771, 20050043219, and 20050158727, the content of each of which is incorporated by reference herein in its entirety). A conjugate may be added to siRNA for any of a number of purposes. For example, the conjugate may be a molecular entity that facilitates the delivery of siRNA into a cell or may be a molecule that comprises a drug or label. Examples of conjugate molecules suitable for attachment to siRNA of the present invention include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423; the content of each of which is incorporated by reference herein in its entirety). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325, the content of each of which is incorporated by reference herein in its entirety. Other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337, incorporated by reference herein in its entirety. Additional examples of conjugate molecules include a hydrophobic group, a membrane active compound, a cell penetrating compound, a cell targeting signal, an interaction modifier, or a steric stabilizer as described in U.S. Patent Publication No. 20040167090, incorporated by reference herein in its entirety. Further examples include the conjugate molecules described in U.S. Patent Publication No. 20050239739, incorporated by reference herein in its entirety.

The type of conjugate used and the extent of conjugation to the siRNA can be evaluated for improved pharmacokinetic profiles, bioavailability, and/or stability of the siRNA while retaining activity. As such, one skilled in the art can screen siRNA molecules having various conjugates attached thereto to identify siRNA conjugates having improved properties using any of a variety of well-known in vitro cell culture or in vivo animal models including the negative-controlled expression studies described above.

A siRNA may be incorporated into carrier systems containing siRNA molecules described herein. The carrier system may be a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system may be a polymer-based carrier system such as a cationic polymer-nucleic acid complex (i.e., polyplex). In additional embodiments, the carrier system can be a cyclodextrin-based carrier system such as a cyclodextrin polymer-nucleic acid complex (see US Patent Application Publication 20070218122, incorporated by reference herein in its entirety). In further embodiments, the carrier system may be a protein-based carrier system such as a cationic peptide-nucleic acid complex. A siRNA molecule may also be delivered as naked siRNA.

In certain embodiments, the carrier system can be a nanoparticle that includes low molecular weight polyethyleneimine (LPEI) or its derivatives (e.g., disulfide cross-linked polyethyleneimine (CLPEI)) and a lipid. The lipid may be a bile acid, such as cholic acid, deoxycholic acid, and lithocholic acid. Such carrier systems are described further in the Examples below. Other exemplary carrier systems are described for example in Wittrup et al. (Nature Reviews/Genetics, 16:543-552, 2015), the content of which is incorporated by reference herein in its entirety.

The compositions of the invention are particularly useful for treating a subject (e.g., a mammalian subject, e.g., human, child or adult) with a chronic liver disease or alcoholic liver disease (ALD). Chronic liver disease refers to diseases of the liver that last over a period of six months. It includes of a wide range of liver pathologies which include inflammation (chronic hepatitis), liver cirrhosis, and hepatocellular carcinoma. Alcoholic liver disease (ALD) typically occurs after years of heavy drinking. Over time, scarring and cirrhosis can occur. Cirrhosis is the final phase of alcoholic liver disease. There may be no symptoms, or symptoms may come on slowly, depending on how well the liver is working. Symptoms tend to be worse after a period of heavy drinking. Early symptoms include: fatigue and loss of energy; poor appetite and weight loss; nausea or belly pain; small, or red spider-like blood vessels on the skin As liver function worsens, symptoms may include: fluid buildup of the legs (edema) and in the abdomen (ascites); yellow color in the skin, mucous membranes, or eyes (jaundice); redness on the palms of the hands; easy bruising and abnormal bleeding; confusion or problems thinking; or pale or clay-colored stools. In men, symptoms may also include impotence, shrinking of the testicles, and breast swelling.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, (e.g., a siRNA or antisense oligonucleotide of the invention) and/or derivative thereof, in combination with a pharmaceutically acceptable carrier.

The effective dosage of each agent can readily be determined by the skilled person, having regard to typical factors each as the age, weight, sex and clinical history of the patient. In general, a suitable daily dose of a compound of the invention will be that amount of the compound which is the lowest dose effective to produce a therapeutic effect. Such an effective dose will generally depend upon the factors described above. Generally, doses of the compounds of this invention for a patient, when used for the indicated effects; will range from about 0.1 mg to about 250 mg per kilogram of body weight per day, more preferably from about 1 mg to about 60 mg per kg per day.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the present invention, or functional derivatives thereof. An "effective amount" is the amount as defined herein in the definition section and refers to an amount effective, at dosages and for periods of time necessary, to achieve the desired therapeutic result, e.g., a diminishment or prevention of effects associated with neuropathic and/or inflammatory pain. A therapeutically effective amount of a compound of the present invention or functional derivatives thereof may vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylactically or therapeutically effective amount is also one in which any toxic or detrimental effects of the compound are outweighed by the beneficial effects.

Dosage regimens may be adjusted to provide the optimum desired response (e.g. a therapeutic or prophylactic response). For example, a single bolus may be administered, several divided doses may be administered over time or the dose may be proportionally reduced or increased as indicated by the exigency of the therapeutic situation. It is especially advantageous to formulate parenteral compositions in dosage unit form for ease of administration and uniformity of dosage. Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the patient.

The term "dosage unit" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound, and (b) the limitations inherent in the art of compounding such an active compound for the treatment of sensitivity in individuals.

In some embodiments, therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is sufficient to reduce or inhibit neuropathic and/or inflammatory pain in a subject. In some embodiments, the therapeutically effective amount is sufficient to eliminate neuropathic and/or inflammatory pain in a subject. Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the compounds of the invention or functional derivatives thereof, and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more compounds of the invention or functional derivatives thereof are optionally tested in one or more appropriate in vitro and/or in vivo animal models of disease, such as models of neuropathic and/or inflammatory pain, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of compounds of the invention or functional derivatives thereof at various concentrations, e.g., as applied to the mass and overall health of the patient. Administration can be accomplished via single or divided doses.

Administering typically involves administering pharmaceutically acceptable dosage forms, which means dosage forms of compounds described herein, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety. Administering may be carried out orally, intradermally, intramuscularly, intraperitoneally, intravenously, subcutaneously, or intranasally. Compounds may be administered alone or with suitable pharmaceutical carriers, and can be in solid or liquid form, such as tablets, capsules, powders, solutions, suspensions, or emulsions.

A pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452 and 4,265,874 (the content of each of which is incorporated by reference herein in its entirety), to form osmotic therapeutic tablets for control release.

Formulations for oral use may also be presented as hard gelatin capsules in which the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Formulations may also include complexes of the parent (unionized) compounds with derivatives of β-cyclodextrin, especially hydroxypropyl-β-cyclodextrin.

An alternative oral formulation can be achieved using a controlled-release formulation, where the compound is encapsulated in an enteric coating.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Each active agent may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions are suitable. Topical application includes the use of mouth washes and gargles.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response, and the like, and are commensurate with a reasonable benefit/risk ratio.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

The PNPLA3 gene rs738409 C>G polymorphism is associated with several types of liver disease (Shen, Journal of Lipid Research, 56:167-175, 2015), the content of which is incorporated by reference herein in its entirety. The G allele is associated with a significantly increased risk of chronic liver disease versus the C allele. Both the GC and GG genotypes are associated with a significantly increased risk of chronic liver disease versus the CC genotype.

Accordingly, the I148M mutation (rs738409 C>G) in the PNPLA3 gene is a strong genetic risk factor for a series of chronic liver diseases, including nonalcoholic/alcoholic fatty liver disease, steatohepatitis, cirrhosis and hepatocellular carcinoma. It has been demonstrated that overexpression of the 148M isoform and not 148I is an important step for the manifestation of these phenotypes. Meanwhile, 148M has been demonstrated as a loss-of-function mutation that reduces the enzymatic activity (triglycerides hydrolase and other unknown function) as compared to the 148I isoform. This indicates that 148M plays a pathogenic role in liver disease etiology in a dominant-negative manner.

Without being limited by any particular theory of mechanism of action, it is believed that reducing the expression of the 148M isoform will lead to reversing disease progress from simple steatosis, steatohepatitis, cirrhosis and even liver cancer. Accordingly, the invention provides siRNA specifically targeting the 148M isoform to reduce its mRNA and protein expression. It has been found that the compositions of the invention have minimal effect on the wild-type 148I isoform. The data herein show that cell lines based model has confirmed that reducing the 148M isoform leads to reduced fat accumulation in human HepG2 cell line.

Example 1: In Vitro Systems for Pharmacological Testing of siRNA Molecules

The present invention identifies a potent siRNA specifically downregulating PNPLA3 148M isoform, namely 148MSi (SEQ ID NO.: 1) and associated sequences SEQ ID NOs: 2 and 278-552. The therapeutic potential of 148MSi may be further characterized through additional testing. To this end: 1) stable cell lines can be established constantly expressing PNPLA3148M-Luc and PNPLA3148I-Luc, which facilitates a subsequent high throughput optimization of 148MSi and its modified analogs in targeting PNPLA3 148M; and 2) The therapeutic effectiveness of 148MSi can be examined in vitro, which can collect key pharmacological parameters to further foster the basis of 148MSi as a therapeutic agent.

To establish stable cell lines and perform a high throughput screening for more candidate siRNA targeting PNPLA3 148M, lentivirus particles may be generated packing the vectors with each of the PNPLA3 148M-Luc and PNPLA3 148I-Luc fusion genes. The virus particles may be transduced into HEK293 cells. Cells constantly expressing the fusion reporter proteins can be selected using puromycin. Following the establishment of these stable cells, a high-throughput screening can be performed to further identify optimal siRNA candidates. Briefly, a series of siRNAs specifically targeting the 148M allele can be designed by altering their length and/or position to target, as well as by artificially introducing mutations into the siRNA sequence. These siRNAs may be transiently transfected into the stable cells to test their specificity and potency by comparing to that of the 148MSi.

It may be that the stable cells are able to serve as an in vitro model for rapid screening of siRNA candidates, which may lead to the identification of other siRNAs possessing equivalent to or even better therapeutic properties than 148MSi. Vectors may be created in the lab and transient transfection may be performed as below.

To examine the therapeutic effectiveness of 148MSi in vitro, the high specificity and potency of 148MSi may be demonstrated, as well as the potential of 148MSi treatment in reducing triglycerides (TG) accumulation (a hallmark of hepatic steatosis) under glucose induction of endogenous PNPLA3 148M in Huh-7 cells (See Examples below). However, glucose treatment may alter many pathways which might confound the effect of PNPLA3. Artificially increasing the PNPLA3 148M expression using adenoviral vectors without integrating into the genome would be useful to examine the focused effect of PNPLA3 148M on the induction of hepatic steatosis. PNPLA3 148M and PNPLA3 148I can be cloned into adenoviral vectors. PNPLA3 148M and PNPLA3 148I adenovirus particles can be generated to transduce the Huh-7 cells, respectively. 148MSi, in a series of concentrations, may be transfected into the cells using Lipofectamine 2000 (Thermal Fisher). The transfected cells can then be treated with free fatty acids (palmitic acid+oleic acid) for 48 hours, and TG accumulation may be measured using Oil Red O staining, and can be further compared between the cells transduced with different PNPLA3 isoforms.

Overexpression of PNPLA3148M isoform may significantly induce TG accumulation as compared to the 148I isoform. Transfection of 148MSi can significantly reduce TG accumulation in a dose-dependent manner and specifically in cells transduced with PNPLA3 148M but not PNPLA3 148I. Although Huh-7 is a PNPLA3 148M homozygote, the expression level of PNPLA3 may be insufficient to induce TG accumulation. Previous studies have shown that overexpression of PNPLA3 148M in hepatocyte indeed increased TG accumulation, and knockdown of PNPLA3 using generic commercial siRNAs can reverse that effect. 148MSi of the invention can outperform generic siRNAs in PNPLA3 148M targeting as shown below and the effect can likely be recapitulated in Huh-7. In one embodiment, short hairpin RNAs (shRNA) for 148MSi can be created and further packaged into adenovirus to perform co-transfection with PNPLA3 adenovirus.

Example 2: siRNA Targeting and Therapeutic Response In Vivo

To validate the cell-based data, useful mouse models can be created for in vivo evaluation of 148MSi. It has been reported that a short-term overexpression of PNPLA3 148M variant using an adenoviral vector leads to ~3 fold increase in hepatic triglycerides. Transgenic mice that overexpress the PNPLA3 148M variant specifically in the liver also causes hepatic steatosis and dysregulated hepatic lipid metabolism. Thus, it is believed that overexpression of PNPLA3 148M variant in mouse liver should provide a useful tool for preclinical testing of the efficacy, pharmacodynamics, and pharmacokinetics.

Figure 7:
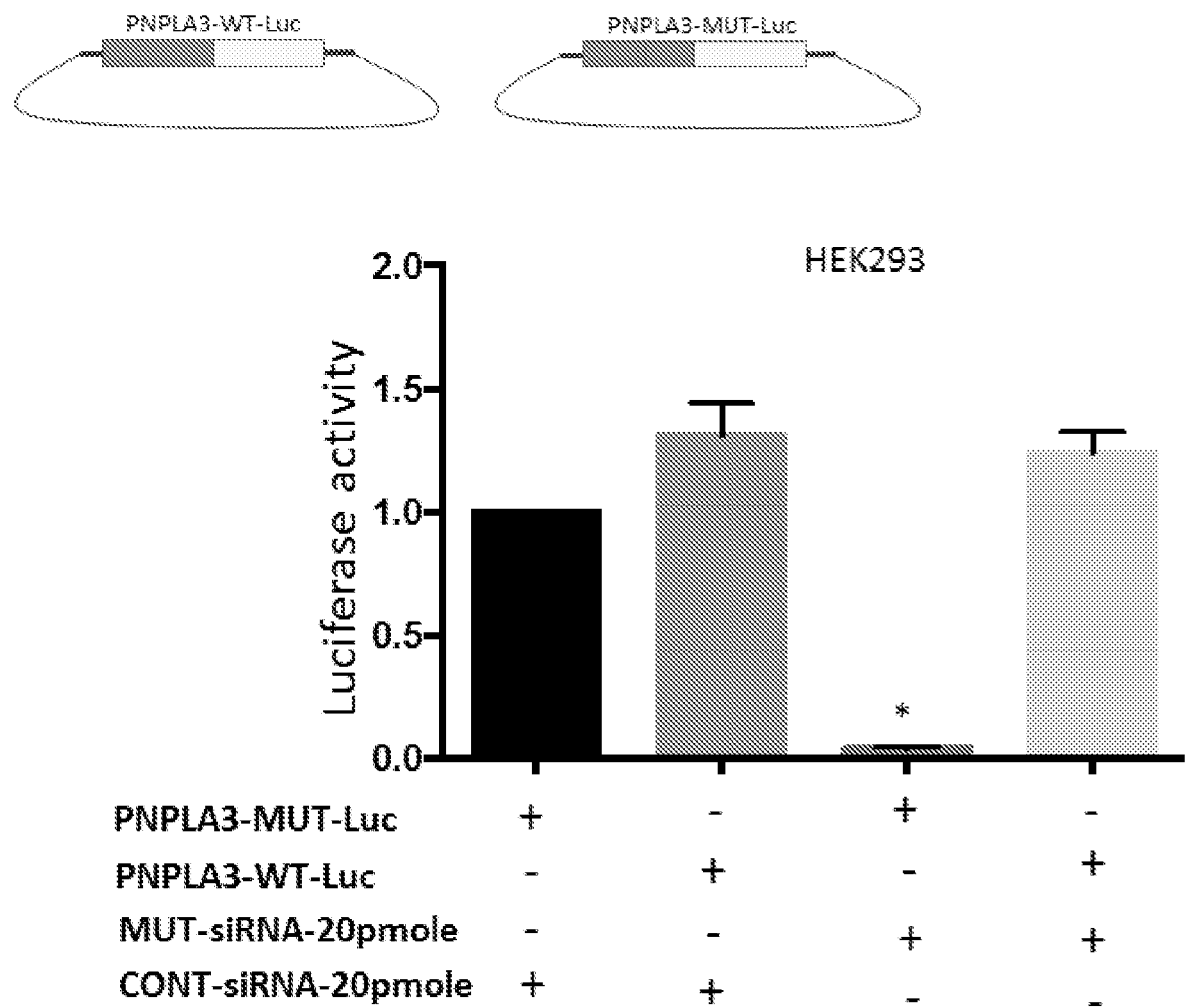
FIG. 7 shows vectors for compositions of the invention and their effectiveness in downregulating the 148M phenotype.

Since adenoviral and lentiviral vectors can efficiently deliver gene products to the liver, their respective features (adenoviral vector does not integrate to the host genome but lentiviral vector does) can be advantageous to the development of both acute and chronic mouse models expressing human PNPLA3 148M (FIG. 7). DNA constructs may be created for both systems, and large preparations can be made for animal injections. In order to validate the two models, PNPLA3 148I or PNPLA3 I148M adenoviruses ($2 \times 10^9$ pfu/mouse) or lentiviruses ($5 \times 10^8$ pfu/mouse) can be injected. For the adenoviral PNPLA3 model, mice may be fasted for 4 hours and sacrificed for blood and liver tissue collection 3 days after the injections. For the lentiviral PNPLA3 model, mice can be sacrificed 1 month after the injections. Serum and hepatic triglycerides and free fatty acids can be analyzed using commercial assay kits (Dako). Hepatic lipid droplets may be analyzed by H&E and Oil Red 0 staining of liver sections. In order to facilitate longitudinal monitoring of the PNPLA3 expression, the two lentiviral vectors that carry PNPLA3 148I-Luc or PNPLA3 148M-Luc fusion gene mentioned in Example 1 above can be used.

Both adenoviral and lentiviral models for PNPLA3148M should develop hepatic steatosis manifested by increased liver triglycerides and lipid droplets. As an alternative strategy, an adeno-associated viral (AAV) vector system may be considered.

For the early phase of in vivo test, the adenoviral model can be used to assess the efficacy of PNPLA3 148M siRNAs. Two days after the adenoviral injection, 148MSi can be delivered using the Invivofectamine 3.0 reagent (Thermo Fisher, 1.5 mg/kg) into mice via tail vein injection. Two days later, animals can be sacrificed for blood and liver tissue collection. PNPLA3 knockdown efficiency may be analyzed by qPCR. Serum and liver TG can be analyzed as described above. To examine the long-term efficacy, the following lentiviral models may be used: PNPLA3 148I, PNPLA3 I148M, PNPLA3 148I-Luc and PNPLA3 148M-Luc. Two regimens can be performed on these 4 models: 1) Injection of 148MSi+Invivofectamine 3.0 (1.5 mg/kg) two days after the lentiviral injection and then weekly injection at a dose of 0.5 mg/kg for 1 month; 2) Injection of 148MSi+Invivofectamine 3.0 4 weeks after the lentiviral injection and then weekly injection at a dose of 0.5 mg/kg for 1 month. The luciferase signal of each mouse can be monitored weekly using, for example the Berthold LB981 NightOwl system (Berthold Technologies GmbH & Co. KG, Germany). For assessing the potential toxicity, we can inject the same doses of siRNAs into wildtype C57BL6/J mice using the same regimens as mentioned above. The mice body weight can be monitored every two days for 1 month. At the end, animals may be euthanized for gross toxicity examination. Liver enzymes (ALT and AST) can be measured and liver histology can be examined.

These animal models should provide useful tools for siRNA tests. According to cellular data, 148MSi should knock down the PNPLA3 148M expression and reverse hepatic steatosis. Although serious toxicity from siRNA/Invivofectamine particles is not expected, any side effect may be noted and minimized by adjusting the dose regimens.

Example 3: Nanoparticle Vectors for siRNA Delivery to the Liver

Delivery of siRNA requires a carrier system that can protect siRNA from enzymatic degradation during circulation, prevent side effects due to non-specific distribution in off-target tissues, and help the siRNA to enter target cells. A ternary gene complex called DPH complex has been reported that includes nucleic acid, polycation (LPEI or disulfide-crosslinked polyethyleneimine, CLPEI), and polysaccharide. That complex has achieved superior gene transfection efficiency to that of commercial gene carriers like Lipofectamine or polyethyleneimine. However, due to its electrostatic nature of the complex, DPH is unstable in circulation and shows suboptimal gene transfection in vivo. It is believed that DPH with greater stability and smaller size can be produced by grafting lipid components to the polycation component such as LPEI (FIG. 2). That belief is supported by the fact that cholesterol grafting reduces the size of polymeric micelle gene carriers from >500 nm to <200 nm by stabilizing the core-shell structure and increases colloidal stability. The lipid modification also facilitates cellular uptake of polyplexes, thereby increasing the gene transfection efficiency. Making a lipid-modified LPEI should help form small (<100 nm) gene carriers, which can stably circulate, effectively reach the liver, and transfect hepatocytes.

Figure 2A:
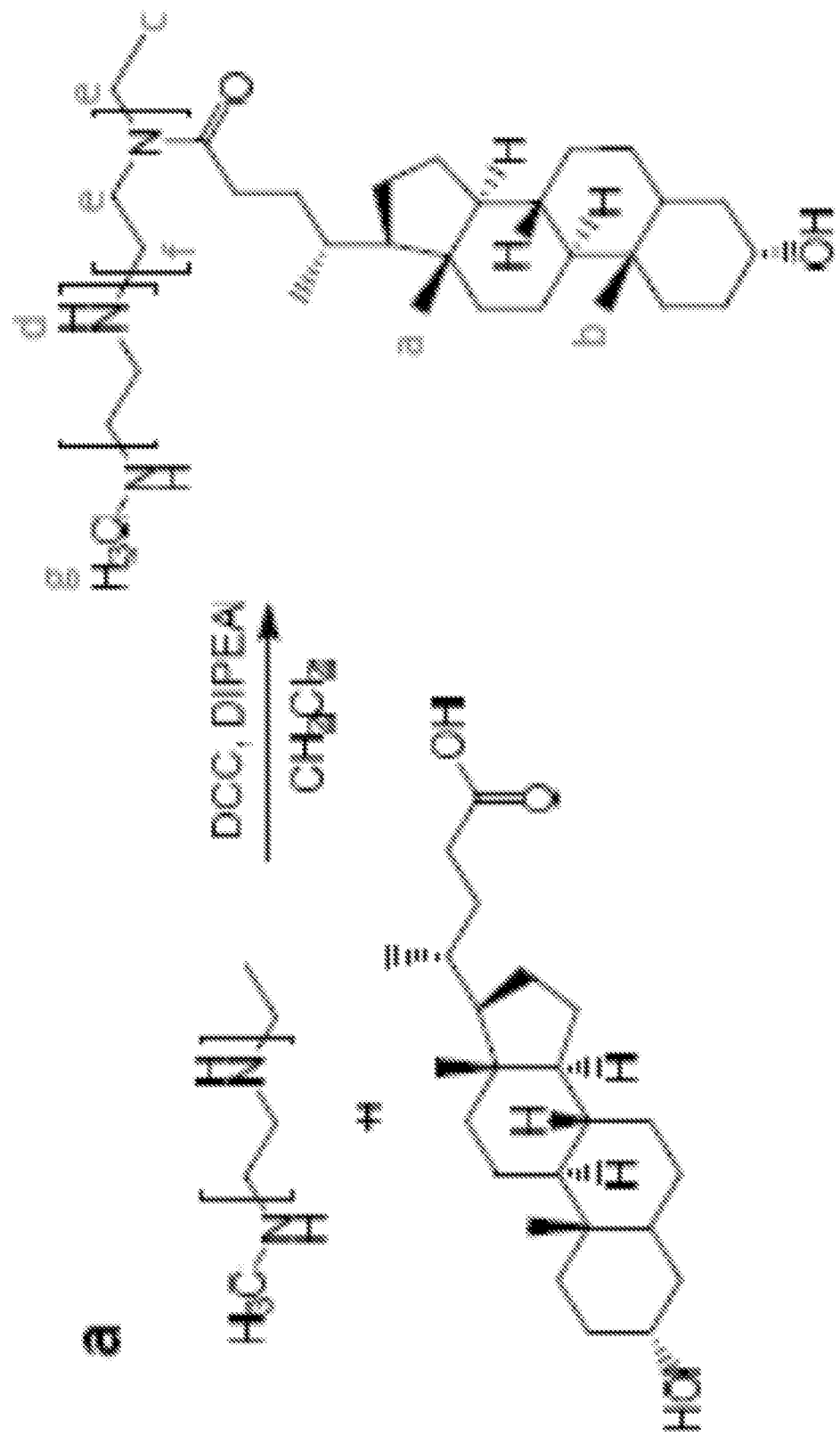
FIG. 2A shows a schematic of lipid-grafted LPEI preparation.
Figure 2B:
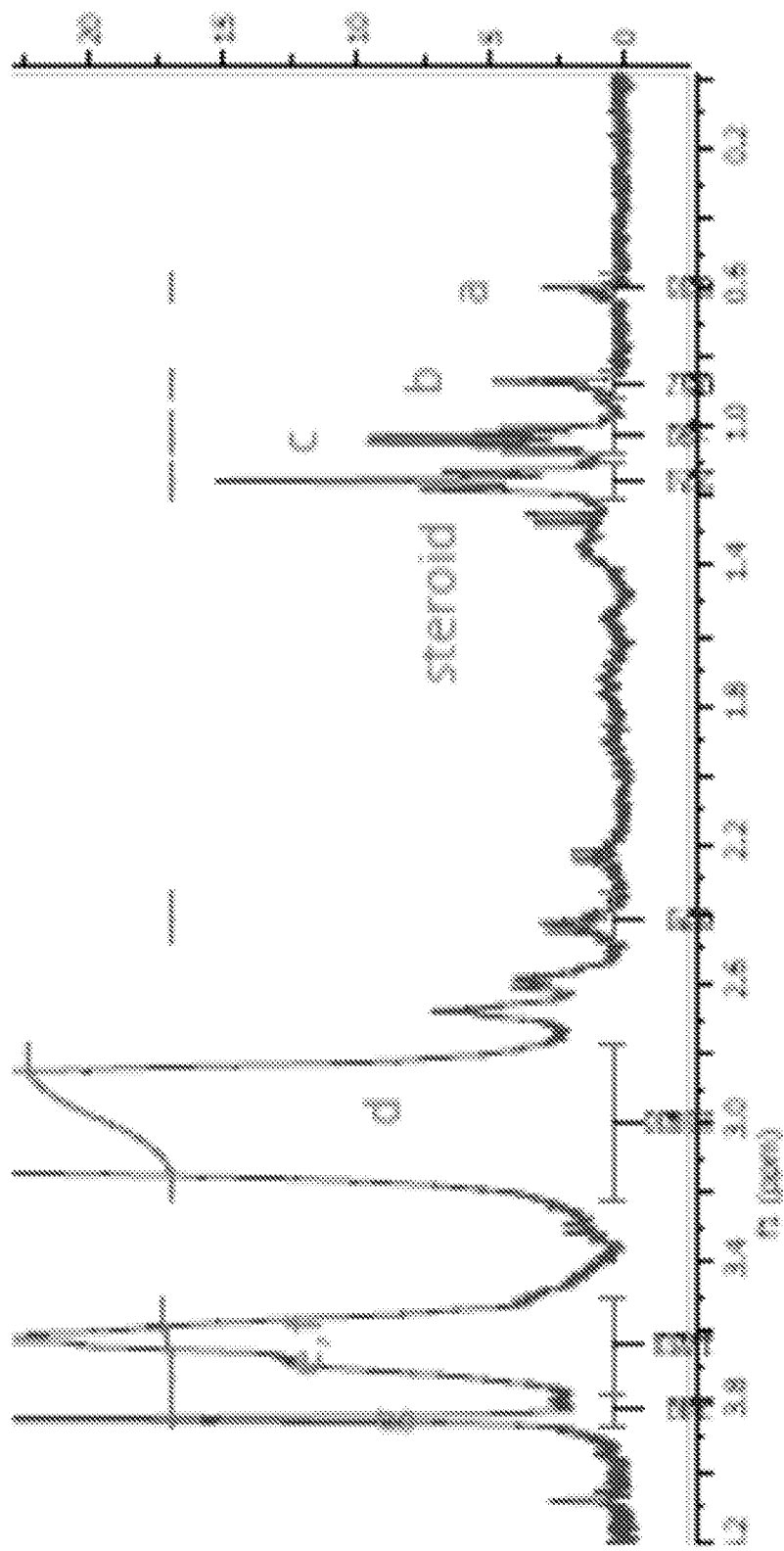
FIG. 2B shows 1H-NMR analysis of a lipid-grafted LPEI preparation.

Bile acids such as cholic acid, deoxycholic acid, and lithocholic acid (LCA), or their derivatives can be used given their biocompatibility, commercial availability, and chemical reactivity. For preparation of lipid-grafted LPEI, bile acids may be grafted as a NHS-activated bile acid to the secondary amine of LPEI (FIG. 2A). A LCA-grafted linear PEI (LPEI), which can be readily translated to conjugates of LCA and LPEI derivatives such as CLPEI, has also been synthesized. It has been confirmed that a ternary complex containing LCA-grafted LPEI (LCA-LPEI) performed better than that with LPEI in reporter gene transfection. The lipid content may be optimized considering its effect on particle stabilization and water solubility. It may be necessary to include a small quantity of water-miscible organic solvent such as DMSO to enhance the solubilization of the components and complex formation. Once a nanoparticulate gene carrier is formed, it is possible to remove the solvent via centrifugal filtration or dialysis. It is possible that the increased stability may interfere with intracellular dissociation of complex. Should this be the case, a lipid may be grafted to the secondary amine via disulfide bond, which can facilitate intracellular dissociation of the lipid. An amine derivative of bile acid may first be reacted with dithiobis [succinimidyl propionate] and then reacted with LPEI in the presence of N,N-diisopropylethylamine. Alternatively, LCA-LPEI can be produced using carbonyldiimidazole (CDA) as a coupling agent. Structures of synthetic intermediates and purified products can be confirmed by 1H-NMR analysis, based on the additional proton shifts indicating the steroid framework in 0.6-1.8 ppm (FIG. 2B).

Ternary complexes of siRNA, LCA-LPEI, and polysaccharides (hyaluronic acid (HA) or dermatan sulfate (DS)) may be formed following methods as shown in Xu, P., Quick, G., Yeo, Y, (2009), Gene delivery through the use of a hyaluronate-associated intracellularly degradable crosslinked polyethyleneimine, Biomaterials, 30(29):5834-5843, incorporated herein by reference in its entirety. Briefly, an siRNA-polymer binary complex may be first formed and then incubated with HA or DS to make a ternary complex. The transfection efficiency of 148Si can be tested in HepG2 cells with the PNPLA3-Luc as a reporter system. The ternary complexes may be characterized with respect to size and surface charge using Zetasizer Nano-ZS90. To examine particle size and its change in serum, the complexes can be incubated in 50% serum solution and sampled at different time points. To estimate chemical stability during circulation, the complexes may be incubated in the presence of serum, nucleases, and heparin (representing anionic glycosaminoglycans). The integrity of ternary complex can be tested with agarose gel electrophoresis as done in previous studies. See, Xu, P., et al., 2009, Gene delivery through the use of a hyaluronate-associated intracellularly degradable crosslinked polyethyleneimine, Biomaterials 30, 5834-5843 and Feng, M., et al., 2014, Stabilization of a hyaluronate-associated gene delivery system using calcium ions, Biomaterials Science, the content of each of which is incorporated by reference herein in its entirety. A complex that does not leach out siRNA upon the challenges may be considered stable. Cellular uptake of the siRNA/LCA-LPEI/HA (or DS) ternary complex can be evaluated with confocal microscopy and flow cytometry using fluorescently labeled siRNA and HepG2 cells. Uptake mechanism may be determined using inhibitors of different endocytosis pathways in each condition and changes in cellular uptake of complexes may be quantified with flow cytometry, and intracellular destination can be identified by co-localizing organelle markers with complexes under a confocal microscope. Cytotoxicity of the complexes may be assessed by incubating HepG2 cells with gene complexes equivalent to 1 to 100 µg/mL CLPEI with a MTT assay and comparing with cells treated with PBS, 148MSi, or LgCLPEI.

Derivatives of cholesterol and LCA have been synthesized. A LCA-grafted linear PEI (LPEI), which can be readily translated to LCA-CLPEI conjugates, has also been synthesized and it has been confirmed that a ternary complex containing LCA-grafted LPEI performed better than that with LPEI in reporter gene transfection. The lipid content may be optimized considering its effect on particle stabilization and water solubility. It may be necessary to include a small quantity of water-miscible organic solvent such as DMSO to enhance the solubilization of the components and complex formation. Once a nanoparticulate gene carrier is formed, it is possible to remove the solvent via centrifugal filtration or dialysis. It is possible that the increased stability may interfere with intracellular dissociation of complex. Should this be the case, a lipid may be grafted to the secondary amine via disulfide bond, which can facilitate intracellular dissociation of the lipid. An amine derivative of bile acid may first be reacted with dithiobis [succinimidyl propionate] and then reacted with CLPEI in the presence of N,N-diisopropylethylamine.

Example 4: Treating a Chronic Liver Disease with Compositions of the Invention

By using various genetic, genomics and systems-based approach, a number of polymorphisms, genes, lipids and miRNAs have been identified that are significantly associated with NAFLD and NASH susceptibility or drug response in treatment of NASH. Specifically for this application, it has been discovered that PNPLA3 148M has a high baseline expression level in human liver due to the linkage disequilibrium of rs738409 G (encoding the 148M isoform) and an intronic expression quantitative trait loci (eQTL) for PNPLA3, which confirms that a high transcription level of PNPLA3 148M is related to an increased risk for NAFLD/NASH.

Figure 4A:
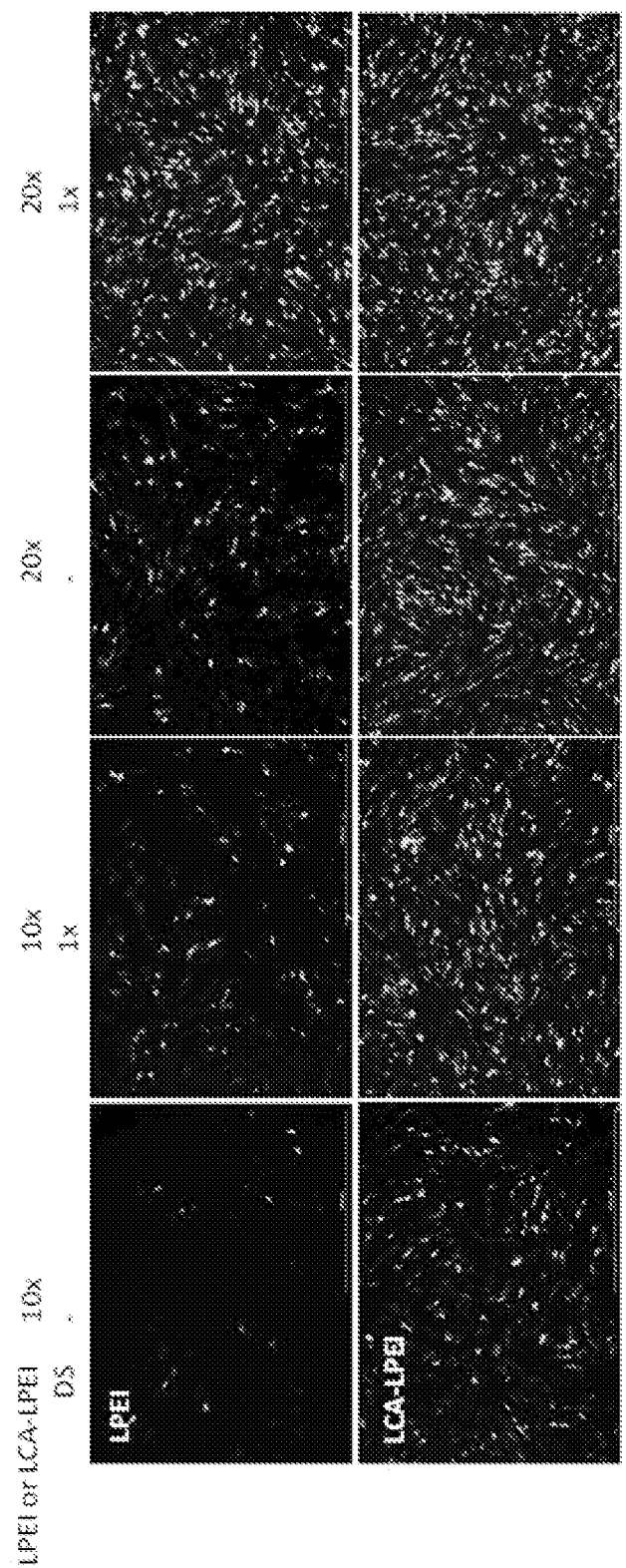
FIGS. 4A-C shows transfection efficiency of LPEI- or LCA-LPEI polyplexes in NIH-3T3 cells. Cells were seeded at a density of 20,000 cells per well in a 24-well plate. After 2 days, cells in each well were treated with polyplexes consisting of pEGFP-C1 plasmid (0.2 µg) and polymers in 10/1 to 20/1 weight ratios±dermatan sulfate (DS, 0.2 µg) and incubated for 48 h. GFP expression was visualized with fluorescence microscope (top panel) and quantified by measuring the fluorescence of the supernatant of cell lysate.
Figure 4B:
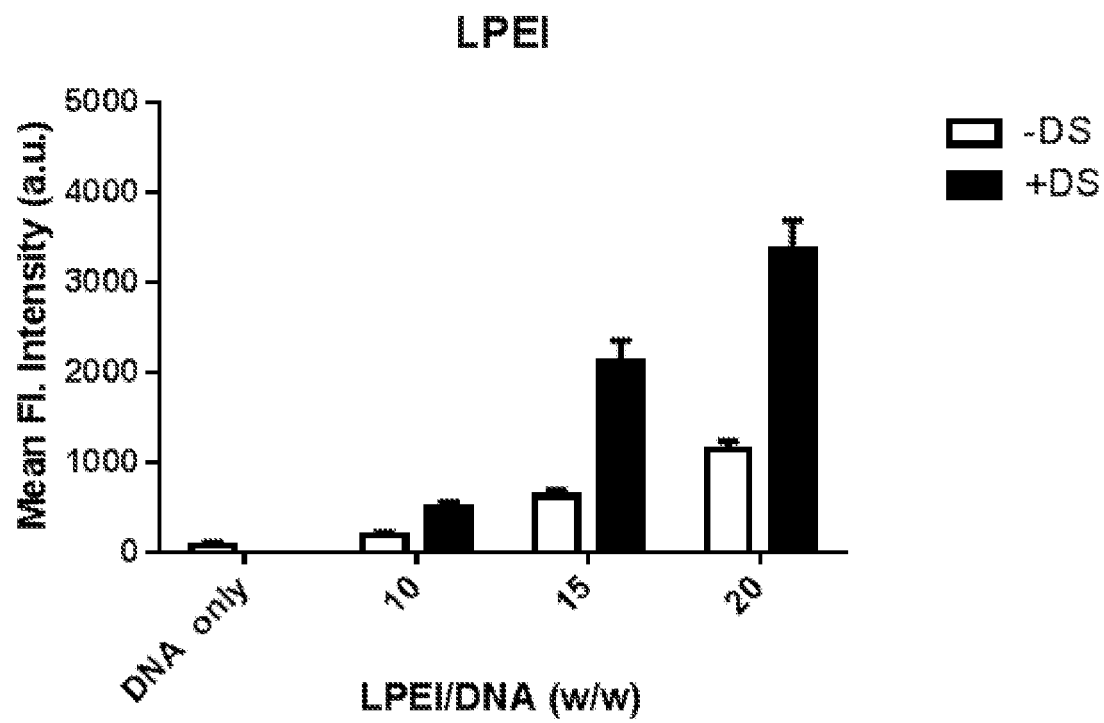
Figure 4C:
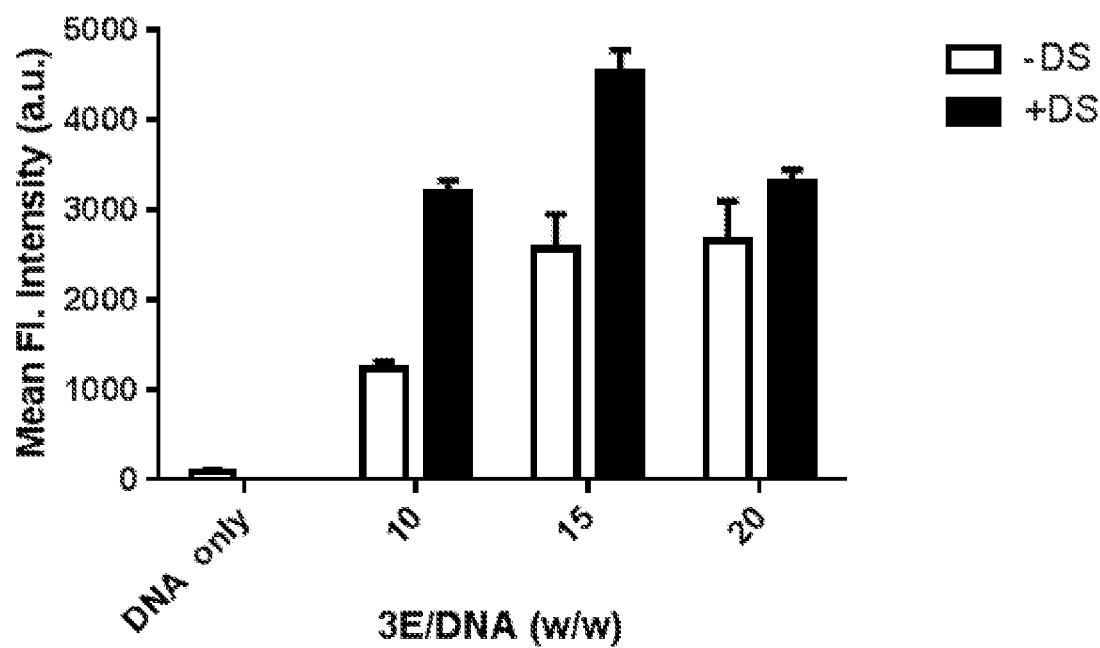

LCA-LPEI has been successfully synthesized as well as a ternary complex of pEGFP, LCA-LPEI, and DS at varying polymer/DNA weight ratios (10/1 to 20/1 w/w). LCA-LPEI has showed greater gene transfection efficiency than LPEI. DS increased transfection for both LPEI and LCA-LPEI polyplexes at all levels of polymer/DNA ratios (FIGS. 4A-C).

Figure 3A:
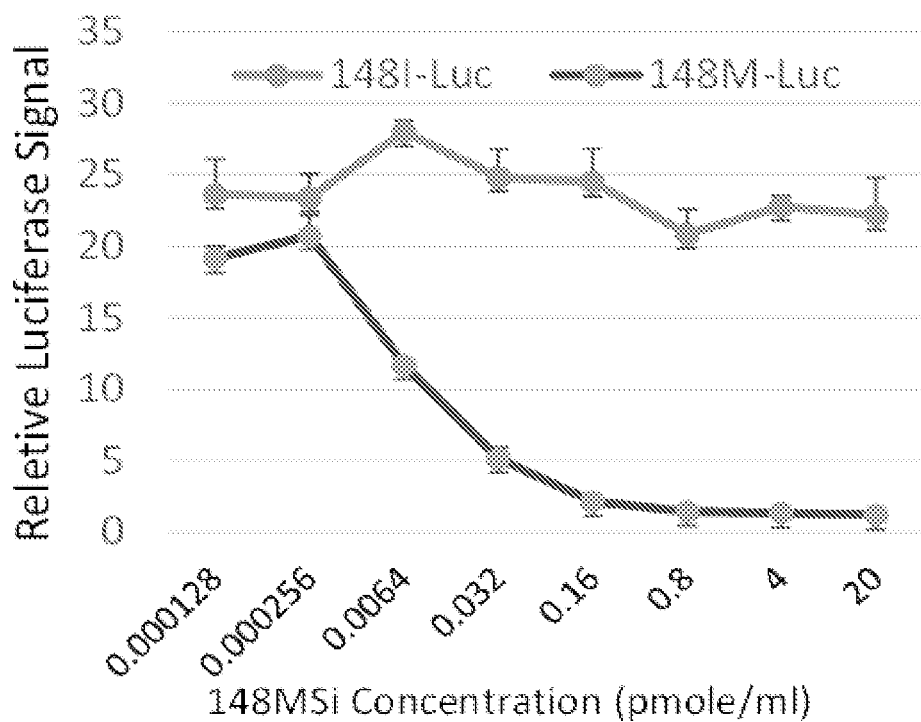
FIG. 3A shows the specificity and potency of 148MSi in targeting PNPLA3148M as compared to PNPLA3 148M with transient transfection of siRNA and PNPLA3-Luc vectors into HEK293 cells for 48 h.
Figure 3B:
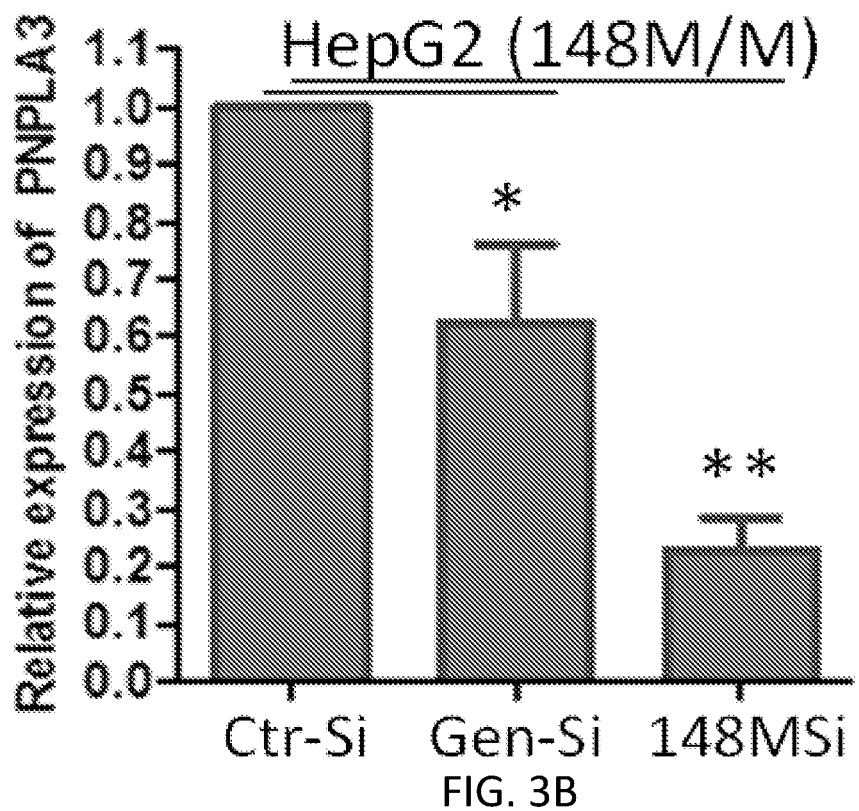
FIGS. 3B and 3C show downregulation of endogenous transcription of PNPLA3 in HepG2 (148M homozygote) and HEK293 (148I homozygote) cells transfected with 20 pmole/ml 148MSi, control (Ctr-Si) or generic PNPLA3 siRNA set (Gen-Si, Santa Cruz) for 48 h.
Figure 3C:
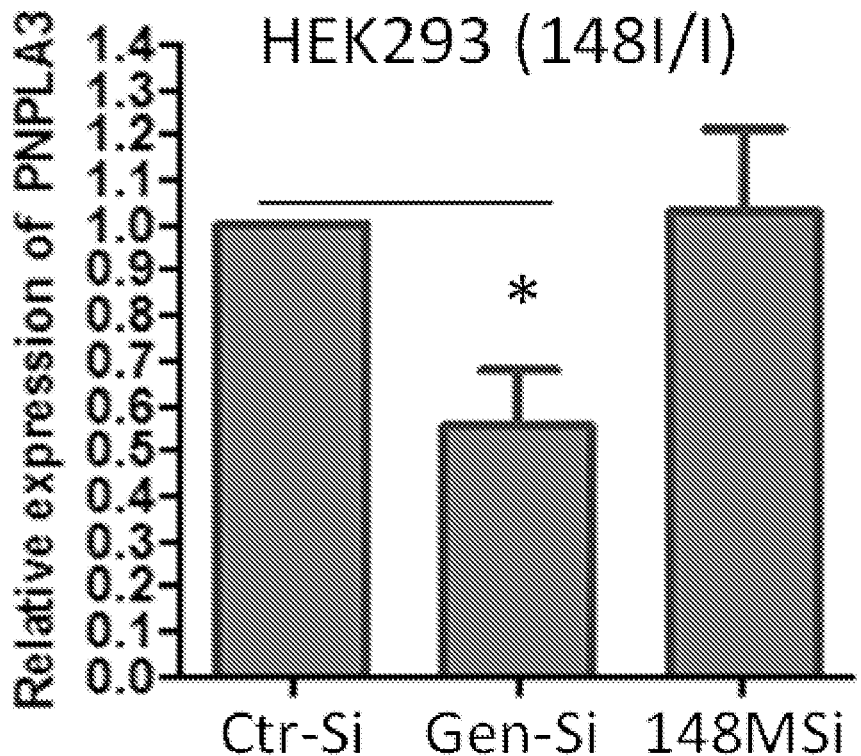
Figure 3D:
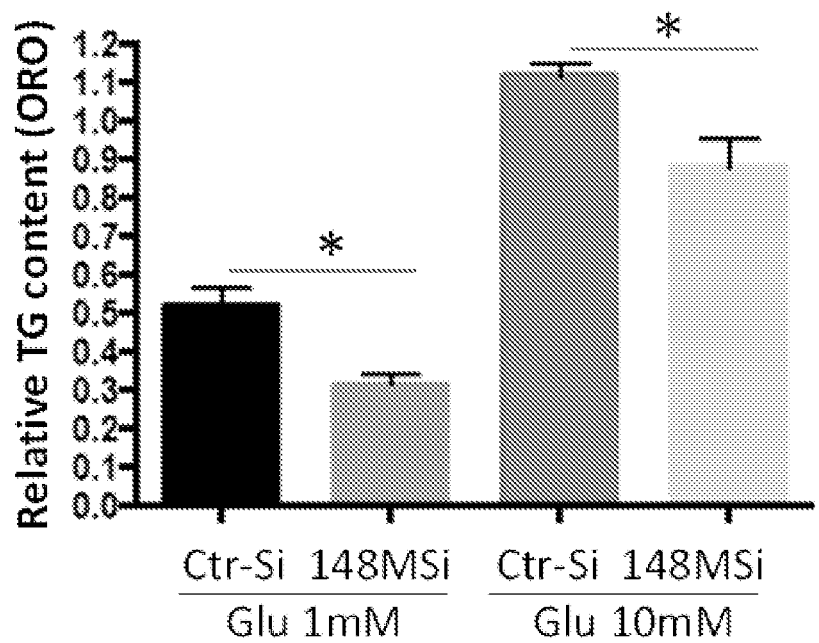
FIGS. 3D-E show reduction of intracellular triglycerides (TG) accumulation (ORO staining) by 148MSi targeting. After transfection, Huh-7 (148M homozygote) cells were co-incubated with free fatty acids [palmitic acid (0.3 mM) and oleic acid (0.9 mM)] and glucose (Glu) at 1 mM or 10 mM concentration for 48 h. *p<0.05; **p<0.01.
Figure 3E:
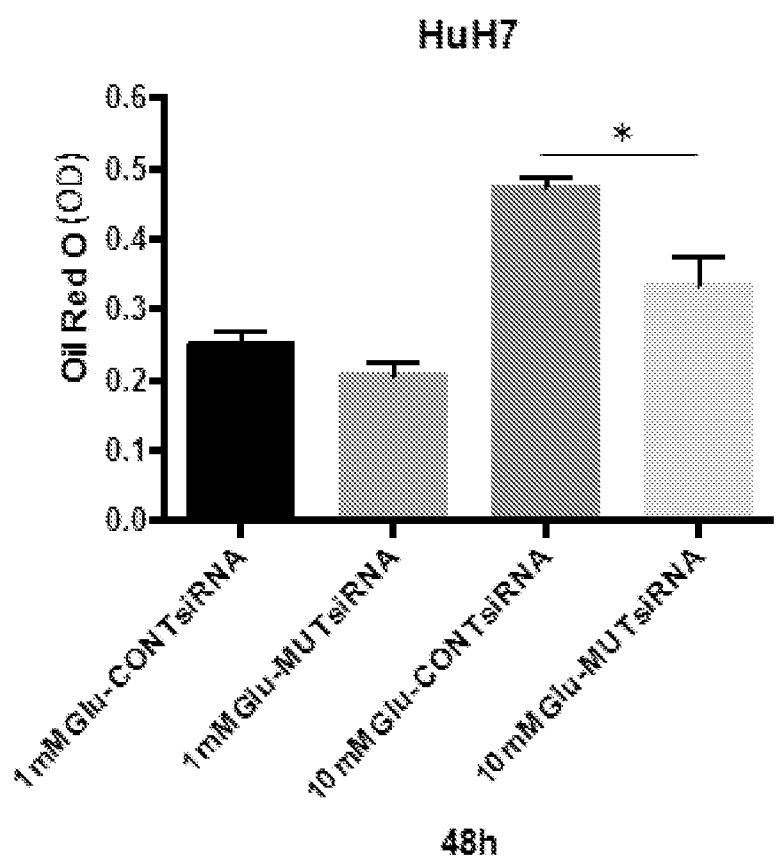

Transient co-transfection of 148MSi and PNPLA3-Luciferase (PNPLA3-Luc) vectors into HEK293 cells has demonstrated that the 148M but not the 148I isoform was significantly down-regulated by 148MSi (FIGS. 3A-C and FIG. 7). This regulation is dose-dependent with a IC50 (50% of mRNA to be cleared) of 8 pM (FIG. 3A). Further analyses demonstrated that 148MSi significantly downregulates endogenous level of PNPLA3 148M mRNA (FIG. 3B) but not the PNPLA3 148I wildtype (FIG. 3C). More importantly, 148MSi transient transfection significantly reduces the TG accumulation in HepG2 cells under induction by glucose (FIGS. 3D-E), as the baseline PNPLA3 expression in HepG2 is insufficient for inducing steatosis. 148MSi as an allele-specific siRNA has outperformed the gene knockdown effect of a commercial PNPLA3 siRNA set (Santa Cruz Biotechnology, Dallas, Tex., a mixture of multiple siRNA with unknown sequences) (FIGS. 3B-C).

Figure 8A:
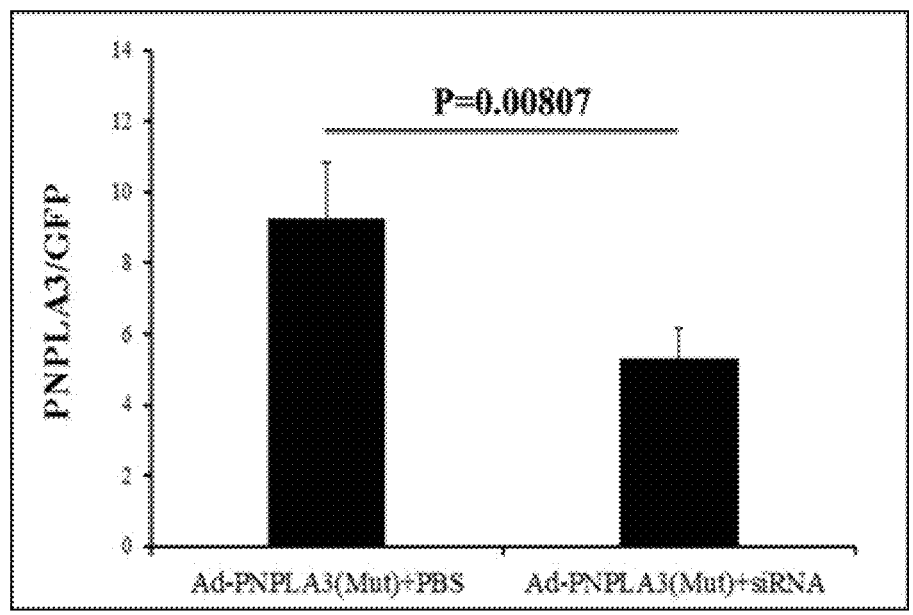
FIGS. 8A-D show in vivo effectiveness of compositions of the invention in reducing hepatic PNPLA3$^{148M}$ expression and total reduction of total hepatic TG levels.
Figure 8B:
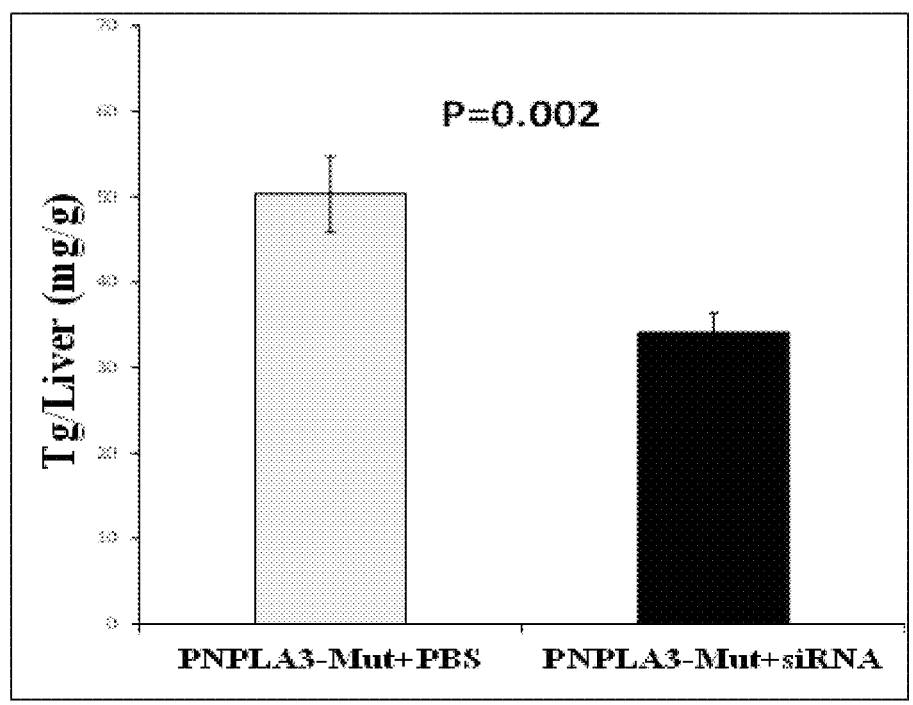
Figure 8C:
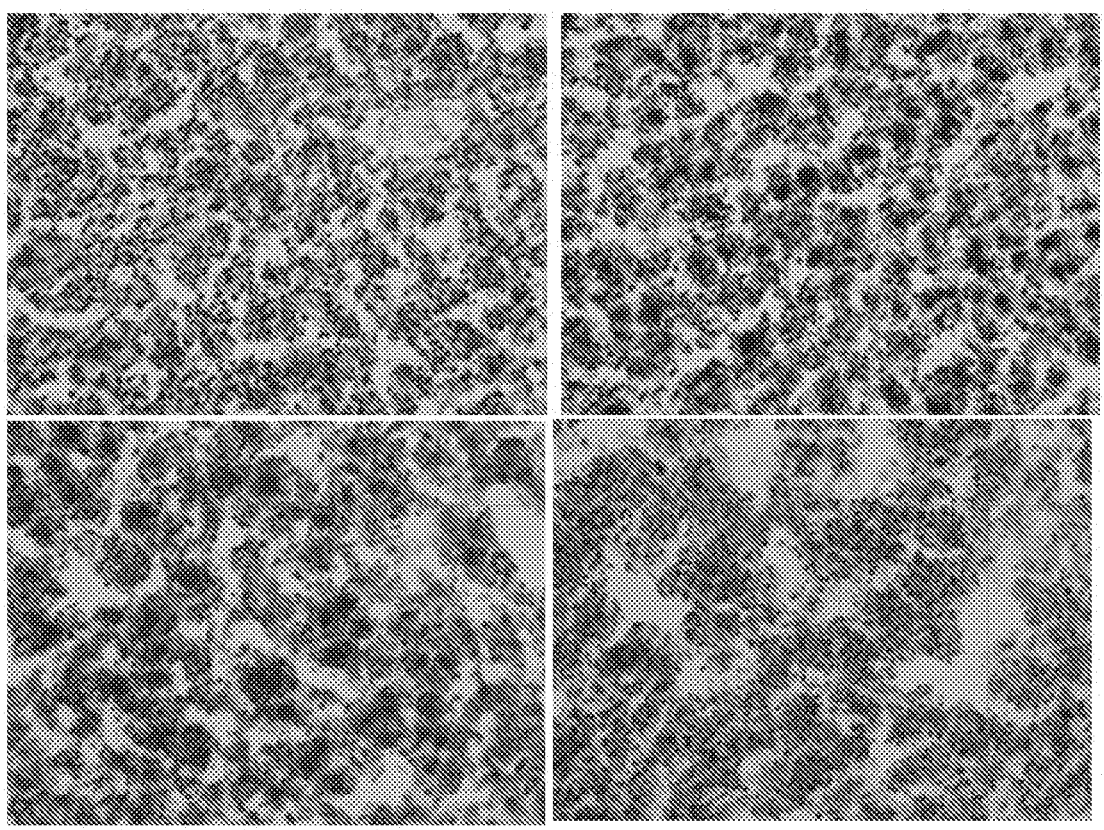
Figure 8D:
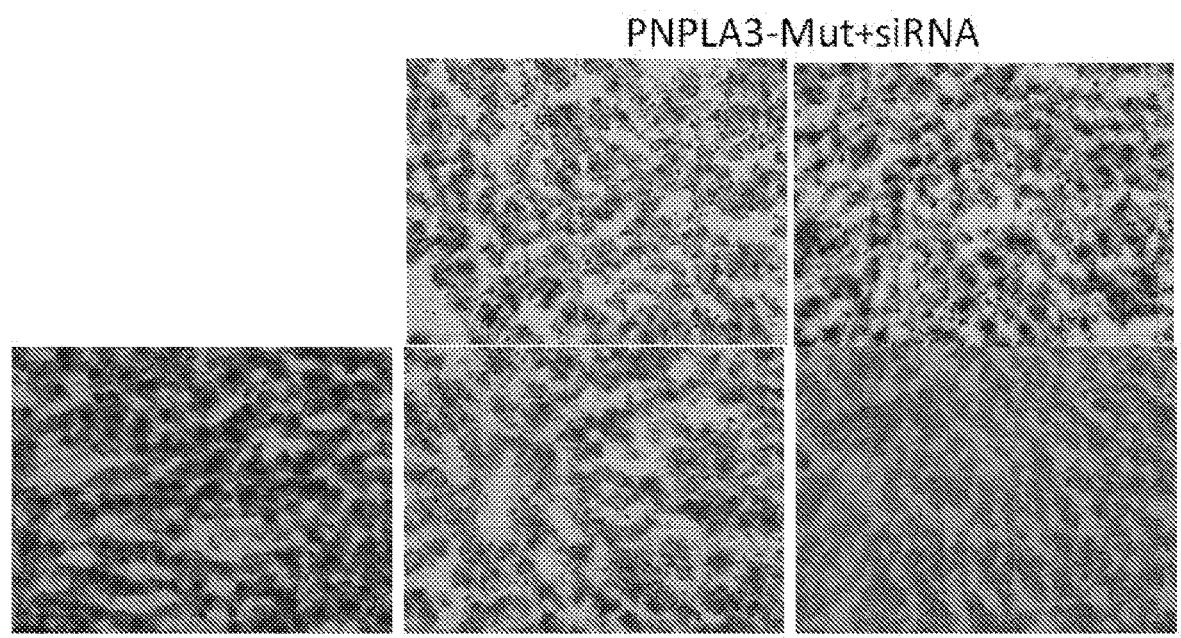

Example 5: Treating a Chronic Liver Disease In Vivo with Compositions of the Invention Compositions of the invention (e.g., mut-specific siRNA) were tested in vivo. The human PNPLA3$^{148M}$ was transduced into mice (n=9) liver via tail-vein injection of adenovirus particles. After 1 week of virus injection, siRNA or PBS (control) that was packed with INVIVOFECTAMINE 3.0 (an animal origin-free lipid nanoparticle designed for high efficiency in vivo delivery of siRNA and miRNA to mouse liver cells following tail vein injection; Thermo Fisher Scientific, Waltham, Mass.) were injected into the mice. Mice were sacrificed after 2 weeks, the human PNPLA3 gene expression as well as total triglycerides (TG) levels in the liver tissue were measured. FIG. 8A shows the significant ($p<0.05$) reduction of hepatic PNPLA3$^{148M}$ expression after siRNA treatment. FIGS. 8B through 8D demonstrated the significant ($p<0.05$) reduction of total hepatic TG levels after siRNA treatment.

What is claimed is:

1. A composition comprising a small interfering RNA (siRNA) molecule that specifically downregulates expression of a rs738409 C>G variant of a patatin-like phospholipase domain-containing (PNPLA3) gene, wherein the siRNA molecule comprises a nucleotide sequence of at least one of SEQ ID NOs 288-297.

2. The composition according to claim 1, further comprising a nanoparticle to which the siRNA molecule is coupled.

3. The composition according to claim 2, wherein the nanoparticle comprises low molecular weight polyethyleneimine (LPEI) and a lipid.

4. The composition according to claim 3, wherein the lipid is a bile acid.

5. The composition according to claim 1, wherein the siRNA molecule does not downregulate expression of a wild-type isoform of the PNPLA3 gene.

6. The composition according to claim 1, wherein the siRNA molecule comprises one or more non-naturally occurring nucleotides.

7. A method for treating a subject with a chronic liver disease or alcoholic liver disease (ALD), the methods comprising administrating a therapeutically effective amount of a composition comprising a small interfering RNA (siRNA) molecule that specifically downregulates expression of a rs738409 C>G variant of a patatin-like phospholipase domain-containing (PNPLA3) gene, wherein the siRNA molecule comprises a nucleotide sequence of at least one of SEQ ID NOs 288-297.

8. The method according to claim 7, wherein the composition further comprises a nanoparticle to which the siRNA molecule is coupled.

9. The method according to claim 8, wherein the nanoparticle comprises low molecular weight polyethyleneimine (LPEI) and a lipid.

10. The method according to claim 9, wherein the lipid is a bile acid.

11. The method according to claim 7, wherein the siRNA molecule comprises one or more non-naturally occurring nucleotides.

* * * * *

SEQUENCE LISTING

```
<160> NUMBER OF SEQ ID NOS: 554

<210> SEQ ID NO 1
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 1
ccugcuucau gccuuucuac agugg                                          25

<210> SEQ ID NO 2
<211> LENGTH: 27
<212> TYPE: RNA
<213> ORGANISM: Artificial Sequence
<220> FEATURE:
<223> OTHER INFORMATION: Synthetic Sequence

<400> SEQUENCE: 2
ccacuguaga aaggcaugaa gcaggaa                                        27

<210> SEQ ID NO 3
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 3
ggccttggta tgttcctgct tcatg                                          25

<210> SEQ ID NO 4
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 4
gccttggtat gttcctgctt catg                                           24

<210> SEQ ID NO 5
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 5
ccttggtatg ttcctgcttc atg                                            23

<210> SEQ ID NO 6
<211> LENGTH: 22
<212> TYPE: DNA
<213> ORGANISM: Artificial Sequence
<220> FEATURE:
<223> OTHER INFORMATION: Synthetic Sequence
```

```
<400> SEQUENCE: 6
cttggtatgt tcctgcttca tg                                              22

<210> SEQ ID NO 7
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 7
ttggtatgtt cctgcttcat g                                               21

<210> SEQ ID NO 8
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 8
tggtatgttc ctgcttcatg                                                 20

<210> SEQ ID NO 9
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 9
ggtatgttcc tgcttcatg                                                  19

<210> SEQ ID NO 10
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 10
gtatgttcct gcttcatg                                                   18

<210> SEQ ID NO 11
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 11
tatgttcctg cttcatg                                                    17

<210> SEQ ID NO 12
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 12
atgttcctgc ttcatg                                                     16

<210> SEQ ID NO 13
<211> LENGTH: 15
```

```
<212> TYPE: DNA
<213> ORGANISM: Artificial Sequence
<220> FEATURE:
<223> OTHER INFORMATION: Synthetic Sequence

<400> SEQUENCE: 13
tgttcctgct tcatg                                                      15

<210> SEQ ID NO 14
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 14
gccttggtat gttcctgctt catgc                                           25

<210> SEQ ID NO 15
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 15
ccttggtatg ttcctgcttc atgc                                            24

<210> SEQ ID NO 16
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 16
cttggtatgt tcctgcttca tgc                                             23

<210> SEQ ID NO 17
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 17
ttggtatgtt cctgcttcat gc                                              22

<210> SEQ ID NO 18
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 18
tggtatgttc ctgcttcatg c                                               21

<210> SEQ ID NO 19
<211> LENGTH: 20
<212> TYPE: DNA
<213> ORGANISM: Artificial Sequence
<220> FEATURE:
<223> OTHER INFORMATION: Syntetic Sequence

<400> SEQUENCE: 19
```
ggtatgttcc tgcttcatgc                                          20

<210> SEQ ID NO 20
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 20
gtatgttcct gcttcatgc                                           19

<210> SEQ ID NO 21
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 21
tatgttcctg cttcatgc                                            18

<210> SEQ ID NO 22
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 22
atgttcctgc ttcatgc                                             17

<210> SEQ ID NO 23
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 23
tgttcctgct tcatgc                                              16

<210> SEQ ID NO 24
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 24
gttcctgctt catgc                                               15

<210> SEQ ID NO 25
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 25
ccttggtatg ttcctgcttc atgcc                                    25

<210> SEQ ID NO 26
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 26
cttggtatgt tcctgcttca tgcc                                          24

<210> SEQ ID NO 27
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 27
ttggtatgtt cctgcttcat gcc                                           23

<210> SEQ ID NO 28
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 28
tggtatgttc ctgcttcatg cc                                            22

<210> SEQ ID NO 29
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 29
ggtatgttcc tgcttcatgc c                                             21

<210> SEQ ID NO 30
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 30
gtatgttcct gcttcatgcc                                               20

<210> SEQ ID NO 31
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 31
tatgttcctg cttcatgcc                                                19

<210> SEQ ID NO 32
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 32
atgttcctgc ttcatgcc                                                 18

<210> SEQ ID NO 33
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 33
tgttcctgct tcatgcc                                                17

<210> SEQ ID NO 34
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 34
gttcctgctt catgcc                                                 16

<210> SEQ ID NO 35
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 35
ttcctgcttc atgcc                                                  15

<210> SEQ ID NO 36
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 36
cttggtatgt tcctgcttca tgcct                                       25

<210> SEQ ID NO 37
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 37
ttggtatgtt cctgcttcat gcct                                        24

<210> SEQ ID NO 38
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 38
tggtatgttc ctgcttcatg cct                                         23

<210> SEQ ID NO 39
<211> LENGTH: 22
<212> TYPE: DNA
<213> ORGANISM: Artificial Sequence
<220> FEATURE:
<223> OTHER INFORMATION: Synthetic Sequence

```
<400> SEQUENCE: 39
ggtatgttcc tgcttcatgc ct                                      22

<210> SEQ ID NO 40
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 40
gtatgttcct gcttcatgcc t                                       21

<210> SEQ ID NO 41
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 41
tatgttcctg cttcatgcct                                         20

<210> SEQ ID NO 42
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 42
atgttcctgc ttcatgcct                                          19

<210> SEQ ID NO 43
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 43
tgttcctgct tcatgcct                                           18

<210> SEQ ID NO 44
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 44
gttcctgctt catgcct                                            17

<210> SEQ ID NO 45
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 45
ttcctgcttc atgcct                                             16

<210> SEQ ID NO 46
```

```
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 46
tcctgcttca tgcct                                                     15

<210> SEQ ID NO 47
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 47
ttggtatgtt cctgcttcat gcctt                                          25

<210> SEQ ID NO 48
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 48
tggtatgttc ctgcttcatg cctt                                           24

<210> SEQ ID NO 49
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 49
ggtatgttcc tgcttcatgc ctt                                            23

<210> SEQ ID NO 50
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 50
gtatgttcct gcttcatgcc tt                                             22

<210> SEQ ID NO 51
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 51
tatgttcctg cttcatgcct t                                              21

<210> SEQ ID NO 52
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 52
```

```
atgttcctgc ttcatgcctt                                              20

<210> SEQ ID NO 53
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 53
tgttcctgct tcatgcctt                                               19

<210> SEQ ID NO 54
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 54
gttcctgctt catgcctt                                                18

<210> SEQ ID NO 55
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 55
ttcctgcttc atgcctt                                                 17

<210> SEQ ID NO 56
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 56
tcctgcttca tgcctt                                                  16

<210> SEQ ID NO 57
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 57
cctgcttcat gcctt                                                   15

<210> SEQ ID NO 58
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 58
tggtatgttc ctgcttcatg ccttt                                        25

<210> SEQ ID NO 59
<211> LENGTH: 24
<212> TYPE: DNA
```

<213> ORGANISM: Artificial Sequence
<220> FEATURE:
<223> OTHER INFORMATION: Synthetic Sequence

<400> SEQUENCE: 59
ggtatgttcc tgcttcatgc cttt                                              24

<210> SEQ ID NO 60
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 60
gtatgttcct gcttcatgcc ttt                                               23

<210> SEQ ID NO 61
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 61
tatgttcctg cttcatgcct tt                                                22

<210> SEQ ID NO 62
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 62
atgttcctgc ttcatgcctt t                                                 21

<210> SEQ ID NO 63
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 63
tgttcctgct tcatgccttt                                                   20

<210> SEQ ID NO 64
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 64
gttcctgctt catgccttt                                                    19

<210> SEQ ID NO 65
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 65
ttcctgcttc atgccttt                                                     18

<210> SEQ ID NO 66
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 66
tcctgcttca tgccttt                                                    17

<210> SEQ ID NO 67
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 67
cctgcttcat gccttt                                                     16

<210> SEQ ID NO 68
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 68
ctgcttcatg ccttt                                                      15

<210> SEQ ID NO 69
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 69
ggtatgttcc tgcttcatgc ctttc                                           25

<210> SEQ ID NO 70
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 70
gtatgttcct gcttcatgcc tttc                                            24

<210> SEQ ID NO 71
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 71
tatgttcctg cttcatgcct ttc                                             23

<210> SEQ ID NO 72
<211> LENGTH: 22
<212> TYPE: DNA
<213> ORGANISM: Artificial Sequence
<220> FEATURE:

<223> OTHER INFORMATION: Synthetic Sequence

<400> SEQUENCE: 72
atgttcctgc ttcatgcctt tc                                           22

<210> SEQ ID NO 73
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 73
tgttcctgct tcatgccttt c                                            21

<210> SEQ ID NO 74
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 74
gttcctgctt catgcctttc                                              20

<210> SEQ ID NO 75
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 75
ttcctgcttc atgcctttc                                               19

<210> SEQ ID NO 76
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 76
tcctgcttca tgcctttc                                                18

<210> SEQ ID NO 77
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 77
cctgcttcat gcctttc                                                 17

<210> SEQ ID NO 78
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 78
ctgcttcatg cctttc                                                  16

```
<210> SEQ ID NO 79
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 79
tgcttcatgc ctttc                                                    15

<210> SEQ ID NO 80
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 80
gtatgttcct gcttcatgcc tttct                                         25

<210> SEQ ID NO 81
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 81
tatgttcctg cttcatgcct ttct                                          24

<210> SEQ ID NO 82
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 82
atgttcctgc ttcatgcctt tct                                           23

<210> SEQ ID NO 83
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 83
tgttcctgct tcatgccttt ct                                            22

<210> SEQ ID NO 84
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 84
gttcctgctt catgcctttc t                                             21

<210> SEQ ID NO 85
<211> LENGTH: 20
<212> TYPE: DNA
<213> ORGANISM: Artificial Sequence
<220> FEATURE:
<223> OTHER INFORMATION: Synthetic Sequence
```

<400> SEQUENCE: 85
ttcctgcttc atgcctttct                                               20

<210> SEQ ID NO 86
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 86
tcctgcttca tgcctttct                                                19

<210> SEQ ID NO 87
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 87
cctgcttcat gcctttct                                                 18

<210> SEQ ID NO 88
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 88
ctgcttcatg cctttct                                                  17

<210> SEQ ID NO 89
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 89
tgcttcatgc ctttct                                                   16

<210> SEQ ID NO 90
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 90
gcttcatgcc tttct                                                    15

<210> SEQ ID NO 91
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 91
tatgttcctg cttcatgcct ttcta                                         25

<210> SEQ ID NO 92
<211> LENGTH: 24

```
<212> TYPE: DNA
<213> ORGANISM: Artificial Sequence
<220> FEATURE:
<223> OTHER INFORMATION: Synthetic Sequence

<400> SEQUENCE: 92
atgttcctgc ttcatgcctt tcta                                              24

<210> SEQ ID NO 93
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 93
tgttcctgct tcatgccttt cta                                               23

<210> SEQ ID NO 94
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 94
gttcctgctt catgcctttc ta                                                22

<210> SEQ ID NO 95
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 95
ttcctgcttc atgcctttct a                                                 21

<210> SEQ ID NO 96
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 96
tcctgcttca tgcctttcta                                                   20

<210> SEQ ID NO 97
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 97
cctgcttcat gcctttcta                                                    19

<210> SEQ ID NO 98
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 98
```

```
ctgcttcatg cctttcta                                                       18
```

<210> SEQ ID NO 99
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 99

```
tgcttcatgc ctttcta                                                        17
```

<210> SEQ ID NO 100
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 100

```
gcttcatgcc tttcta                                                         16
```

<210> SEQ ID NO 101
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 101

```
cttcatgcct ttcta                                                          15
```

<210> SEQ ID NO 102
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 102

```
atgttcctgc ttcatgcctt tctac                                               25
```

<210> SEQ ID NO 103
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 103

```
tgttcctgct tcatgccttt ctac                                                24
```

<210> SEQ ID NO 104
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 104

```
gttcctgctt catgcctttc tac                                                 23
```

<210> SEQ ID NO 105
<211> LENGTH: 22
<212> TYPE: DNA
<213> ORGANISM: Artificial Sequence

```
<220> FEATURE:
<223> OTHER INFORMATION: Synthetic Sequence

<400> SEQUENCE: 105
ttcctgcttc atgcctttct ac                                              22

<210> SEQ ID NO 106
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 106
tcctgcttca tgcctttcta c                                               21

<210> SEQ ID NO 107
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 107
cctgcttcat gcctttctac                                                 20

<210> SEQ ID NO 108
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 108
ctgcttcatg cctttctac                                                  19

<210> SEQ ID NO 109
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 109
tgcttcatgc ctttctac                                                   18

<210> SEQ ID NO 110
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 110
gcttcatgcc tttctac                                                    17

<210> SEQ ID NO 111
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 111
cttcatgcct ttctac                                                     16
```

<210> SEQ ID NO 112
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 112
ttcatgcctt tctac                                                    15

<210> SEQ ID NO 113
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 113
tgttcctgct tcatgccttt ctaca                                         25

<210> SEQ ID NO 114
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 114
gttcctgctt catgcctttc taca                                          24

<210> SEQ ID NO 115
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 115
ttcctgcttc atgcctttct aca                                           23

<210> SEQ ID NO 116
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 116
tcctgcttca tgcctttcta ca                                            22

<210> SEQ ID NO 117
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 117
cctgcttcat gctttctac a                                              21

<210> SEQ ID NO 118
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 118
ctgcttcatg cctttctaca                                      20

<210> SEQ ID NO 119
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 119
tgcttcatgc ctttctaca                                       19

<210> SEQ ID NO 120
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 120
gcttcatgcc tttctaca                                        18

<210> SEQ ID NO 121
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 121
cttcatgcct ttctaca                                         17

<210> SEQ ID NO 122
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 122
ttcatgcctt tctaca                                          16

<210> SEQ ID NO 123
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 123
tcatgccttt ctaca                                           15

<210> SEQ ID NO 124
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 124
gttcctgctt catgcctttc tacag                                25

<210> SEQ ID NO 125

```
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 125
ttcctgcttc atgcctttct acag                                          24

<210> SEQ ID NO 126
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 126
tcctgcttca tgcctttcta cag                                           23

<210> SEQ ID NO 127
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 127
cctgcttcat gcctttctac ag                                            22

<210> SEQ ID NO 128
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 128
ctgcttcatg cctttctaca g                                             21

<210> SEQ ID NO 129
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 129
tgcttcatgc ctttctacag                                               20

<210> SEQ ID NO 130
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 130
gcttcatgcc tttctacag                                                19

<210> SEQ ID NO 131
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 131
```
cttcatgcct ttctacag          18

<210> SEQ ID NO 132
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 132
ttcatgcctt tctacag           17

<210> SEQ ID NO 133
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 133
tcatgccttt ctacag            16

<210> SEQ ID NO 134
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 134
catgcctttc tacag             15

<210> SEQ ID NO 135
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 135
ttcctgcttc atgcctttct acagt   25

<210> SEQ ID NO 136
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 136
tcctgcttca tgcctttcta cagt    24

<210> SEQ ID NO 137
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 137
cctgcttcat gcctttctac agt     23

<210> SEQ ID NO 138
<211> LENGTH: 22
<212> TYPE: DNA

```
<213> ORGANISM: Artificial Sequence
<220> FEATURE:
<223> OTHER INFORMATION: Synthetic Sequence

<400> SEQUENCE: 138
ctgcttcatg cctttctaca gt                                              22

<210> SEQ ID NO 139
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 139
tgcttcatgc ctttctacag t                                               21

<210> SEQ ID NO 140
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 140
gcttcatgcc tttctacagt                                                 20

<210> SEQ ID NO 141
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 141
cttcatgcct ttctacagt                                                  19

<210> SEQ ID NO 142
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 142
ttcatgcctt tctacagt                                                   18

<210> SEQ ID NO 143
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 143
tcatgccttt ctacagt                                                    17

<210> SEQ ID NO 144
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 144
catgcctttc tacagt                                                     16
```

<210> SEQ ID NO 145
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 145
atgcctttct acagt                                                      15

<210> SEQ ID NO 146
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 146
tcctgcttca tgcctttcta cagtg                                           25

<210> SEQ ID NO 147
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 147
cctgcttcat gcctttctac agtg                                            24

<210> SEQ ID NO 148
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 148
ctgcttcatg cctttctaca gtg                                             23

<210> SEQ ID NO 149
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 149
tgcttcatgc ctttctacag tg                                              22

<210> SEQ ID NO 150
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 150
gcttcatgcc tttctacagt g                                               21

<210> SEQ ID NO 151
<211> LENGTH: 20
<212> TYPE: DNA
<213> ORGANISM: Artificial Sequence
<220> FEATURE:

<223> OTHER INFORMATION: Synthetic Sequence

<400> SEQUENCE: 151
cttcatgcct ttctacagtg                                                   20

<210> SEQ ID NO 152
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 152
ttcatgcctt tctacagtg                                                    19

<210> SEQ ID NO 153
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 153
tcatgccttt ctacagtg                                                     18

<210> SEQ ID NO 154
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 154
catgcctttc tacagtg                                                      17

<210> SEQ ID NO 155
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 155
atgcctttct acagtg                                                       16

<210> SEQ ID NO 156
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 156
tgcctttcta cagtg                                                        15

<210> SEQ ID NO 157
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 157
cctgcttcat gcctttctac agtgg                                             25

<210> SEQ ID NO 158
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 158
ctgcttcatg cctttctaca gtgg                                    24

<210> SEQ ID NO 159
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 159
tgcttcatgc ctttctacag tgg                                     23

<210> SEQ ID NO 160
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 160
gcttcatgcc tttctacagt gg                                      22

<210> SEQ ID NO 161
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 161
cttcatgcct ttctacagtg g                                       21

<210> SEQ ID NO 162
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 162
ttcatgcctt tctacagtgg                                         20

<210> SEQ ID NO 163
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 163
tcatgccttt ctacagtgg                                          19

<210> SEQ ID NO 164
<211> LENGTH: 18
<212> TYPE: DNA
<213> ORGANISM: Artificial Sequence
<220> FEATURE:
<223> OTHER INFORMATION: Synthetic Sequence

```
<400> SEQUENCE: 164
catgcctttc tacagtgg                                              18

<210> SEQ ID NO 165
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 165
atgcctttct acagtgg                                               17

<210> SEQ ID NO 166
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 166
tgcctttcta cagtgg                                                16

<210> SEQ ID NO 167
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 167
gcctttctac agtgg                                                 15

<210> SEQ ID NO 168
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 168
ctgcttcatg cctttctaca gtggc                                      25

<210> SEQ ID NO 169
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 169
tgcttcatgc ctttctacag tggc                                       24

<210> SEQ ID NO 170
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 170
gcttcatgcc tttctacagt ggc                                        23

<210> SEQ ID NO 171
<211> LENGTH: 22
```

```
<212> TYPE: DNA
<213> ORGANISM: Artificial Sequence
<220> FEATURE:
<223> OTHER INFORMATION: Synthetic Sequence

<400> SEQUENCE: 171
cttcatgcct ttctacagtg gc                                               22

<210> SEQ ID NO 172
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 172
ttcatgcctt tctacagtgg c                                                21

<210> SEQ ID NO 173
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 173
tcatgccttt ctacagtggc                                                  20

<210> SEQ ID NO 174
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 174
catgcctttc tacagtggc                                                   19

<210> SEQ ID NO 175
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 175
atgcctttct acagtggc                                                    18

<210> SEQ ID NO 176
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 176
tgcctttcta cagtggc                                                     17

<210> SEQ ID NO 177
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 177
```

```
gcctttctac agtggc                                                    16

<210> SEQ ID NO 178
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 178
cctttctaca gtggc                                                     15

<210> SEQ ID NO 179
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 179
tgcttcatgc ctttctacag tggcc                                          25

<210> SEQ ID NO 180
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 180
gcttcatgcc tttctacagt ggcc                                           24

<210> SEQ ID NO 181
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 181
cttcatgcct ttctacagtg gcc                                            23

<210> SEQ ID NO 182
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 182
ttcatgcctt tctacagtgg cc                                             22

<210> SEQ ID NO 183
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 183
tcatgccttt ctacagtggc c                                              21

<210> SEQ ID NO 184
<211> LENGTH: 20
<212> TYPE: DNA
<213> ORGANISM: Artificial Sequence
```

```
<220> FEATURE:
<223> OTHER INFORMATION: Synthetic Sequence

<400> SEQUENCE: 184
catgcctttc tacagtggcc                                               20

<210> SEQ ID NO 185
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 185
atgcctttct acagtggcc                                                19

<210> SEQ ID NO 186
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 186
tgcctttcta cagtggcc                                                 18

<210> SEQ ID NO 187
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 187
gcctttctac agtggcc                                                  17

<210> SEQ ID NO 188
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 188
cctttctaca gtggcc                                                   16

<210> SEQ ID NO 189
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 189
ctttctacag tggcc                                                    15

<210> SEQ ID NO 190
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 190
gcttcatgcc tttctacagt ggcct                                         25
```

```
<210> SEQ ID NO 191
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 191
cttcatgcct ttctacagtg gcct                                          24

<210> SEQ ID NO 192
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 192
ttcatgcctt tctacagtgg cct                                           23

<210> SEQ ID NO 193
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 193
tcatgccttt ctacagtggc ct                                            22

<210> SEQ ID NO 194
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 194
catgcctttc tacagtggcc t                                             21

<210> SEQ ID NO 195
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 195
atgcctttct acagtggcct                                               20

<210> SEQ ID NO 196
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 196
tgcctttcta cagtggcct                                                19

<210> SEQ ID NO 197
<211> LENGTH: 18
<212> TYPE: DNA
<213> ORGANISM: Artificial Sequence
<220> FEATURE:
<223> OTHER INFORMATION: Synthetic Sequence
```

-continued

<400> SEQUENCE: 197
gcctttctac agtggcct                                                         18

<210> SEQ ID NO 198
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 198
cctttctaca gtggcct                                                          17

<210> SEQ ID NO 199
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 199
ctttctacag tggcct                                                           16

<210> SEQ ID NO 200
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 200
tttctacagt ggcct                                                            15

<210> SEQ ID NO 201
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 201
cttcatgcct ttctacagtg gcctt                                                 25

<210> SEQ ID NO 202
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 202
ttcatgcctt tctacagtgg cctt                                                  24

<210> SEQ ID NO 203
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 203
tcatgccttt ctacagtggc ctt                                                   23

<210> SEQ ID NO 204

```
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 204
catgcctttc tacagtggcc tt                                                  22

<210> SEQ ID NO 205
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 205
atgcctttct acagtggcct t                                                   21

<210> SEQ ID NO 206
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 206
tgcctttcta cagtggcctt                                                     20

<210> SEQ ID NO 207
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 207
gcctttctac agtggcctt                                                      19

<210> SEQ ID NO 208
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 208
cctttctaca gtggcctt                                                       18

<210> SEQ ID NO 209
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 209
ctttctacag tggcctt                                                        17

<210> SEQ ID NO 210
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 210
```
tttctacagt ggcctt                                                              16

<210> SEQ ID NO 211
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 211
ttctacagtg gcctt                                                               15

<210> SEQ ID NO 212
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 212
ttcatgcctt tctacagtgg cctta                                                    25

<210> SEQ ID NO 213
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 213
tcatgccttt ctacagtggc ctta                                                     24

<210> SEQ ID NO 214
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 214
catgcctttc tacagtggcc tta                                                      23

<210> SEQ ID NO 215
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 215
atgcctttct acagtggcct ta                                                       22

<210> SEQ ID NO 216
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 216
tgcctttcta cagtggcctt a                                                        21

<210> SEQ ID NO 217
<211> LENGTH: 20
<212> TYPE: DNA

```
<213> ORGANISM: Artificial Sequence
<220> FEATURE:
<223> OTHER INFORMATION: Synthetic Sequence

<400> SEQUENCE: 217
gcctttctac agtggcctta                                             20

<210> SEQ ID NO 218
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 218
cctttctaca gtggcctta                                              19

<210> SEQ ID NO 219
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 219
ctttctacag tggcctta                                               18

<210> SEQ ID NO 220
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 220
tttctacagt ggcctta                                                17

<210> SEQ ID NO 221
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 221
ttctacagtg gcctta                                                 16

<210> SEQ ID NO 222
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 222
tctacagtgg cctta                                                  15

<210> SEQ ID NO 223
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 223
tcatgccttt ctacagtggc cttat                                       25
```

<210> SEQ ID NO 224
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 224
catgcctttc tacagtggcc ttat                                          24

<210> SEQ ID NO 225
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 225
atgcctttct acagtggcct tat                                           23

<210> SEQ ID NO 226
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 226
tgcctttcta cagtggcctt at                                            22

<210> SEQ ID NO 227
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 227
gcctttctac agtggcctta t                                             21

<210> SEQ ID NO 228
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 228
cctttctaca gtggccttat                                               20

<210> SEQ ID NO 229
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 229
ctttctacag tggccttat                                                19

<210> SEQ ID NO 230
<211> LENGTH: 18
<212> TYPE: DNA
<213> ORGANISM: Artificial Sequence
<220> FEATURE:

```
<223> OTHER INFORMATION: Synthetic Sequence

<400> SEQUENCE: 230
tttctacagt ggccttat                                                      18

<210> SEQ ID NO 231
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 231
ttctacagtg gccttat                                                       17

<210> SEQ ID NO 232
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 232
tctacagtgg ccttat                                                        16

<210> SEQ ID NO 233
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 233
ctacagtggc cttat                                                         15

<210> SEQ ID NO 234
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 234
catgcctttc tacagtggcc ttatc                                              25

<210> SEQ ID NO 235
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 235
atgcctttct acagtggcct tatc                                               24

<210> SEQ ID NO 236
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 236
tgcctttcta cagtggcctt atc                                                23
```

```
<210> SEQ ID NO 237
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 237
gcctttctac agtggcctta tc                                              22

<210> SEQ ID NO 238
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 238
cctttctaca gtggccttat c                                               21

<210> SEQ ID NO 239
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 239
ctttctacag tggccttatc                                                 20

<210> SEQ ID NO 240
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 240
tttctacagt ggccttatc                                                  19

<210> SEQ ID NO 241
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 241
ttctacagtg gccttatc                                                   18

<210> SEQ ID NO 242
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 242
tctacagtgg ccttatc                                                    17

<210> SEQ ID NO 243
<211> LENGTH: 16
<212> TYPE: DNA
<213> ORGANISM: Artificial Sequence
<220> FEATURE:
<223> OTHER INFORMATION: Synthetic Sequence
```

<400> SEQUENCE: 243
ctacagtggc cttatc                                            16

<210> SEQ ID NO 244
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 244
tacagtggcc ttatc                                             15

<210> SEQ ID NO 245
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 245
atgcctttct acagtggcct tatcc                                  25

<210> SEQ ID NO 246
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 246
tgcctttcta cagtggcctt atcc                                   24

<210> SEQ ID NO 247
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 247
gcctttctac agtggcctta tcc                                    23

<210> SEQ ID NO 248
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 248
cctttctaca gtggccttat cc                                     22

<210> SEQ ID NO 249
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 249
ctttctacag tggccttatc c                                      21

<210> SEQ ID NO 250
<211> LENGTH: 20

<212> TYPE: DNA
<213> ORGANISM: Artificial Sequence
<220> FEATURE:
<223> OTHER INFORMATION: Synthetic Sequence

<400> SEQUENCE: 250
tttctacagt ggccttatcc                                        20

<210> SEQ ID NO 251
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 251
ttctacagtg gccttatcc                                         19

<210> SEQ ID NO 252
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 252
tctacagtgg ccttatcc                                          18

<210> SEQ ID NO 253
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 253
ctacagtggc cttatcc                                           17

<210> SEQ ID NO 254
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 254
tacagtggcc ttatcc                                            16

<210> SEQ ID NO 255
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 255
acagtggcct tatcc                                             15

<210> SEQ ID NO 256
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 256 tgccttttcta cagtggcctt atccc                                            25

<210> SEQ ID NO 257
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 257
gcctttctac agtggcctta tccc                                              24

<210> SEQ ID NO 258
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 258
cctttctaca gtggccttat ccc                                               23

<210> SEQ ID NO 259
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 259
ctttctacag tggccttatc cc                                                22

<210> SEQ ID NO 260
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 260
tttctacagt ggccttatcc c                                                 21

<210> SEQ ID NO 261
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 261
ttctacagtg gccttatccc                                                   20

<210> SEQ ID NO 262
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 262
tctacagtgg ccttatccc                                                    19

<210> SEQ ID NO 263
<211> LENGTH: 18
<212> TYPE: DNA
<213> ORGANISM: Artificial Sequence

```
<220> FEATURE:
<223> OTHER INFORMATION: Synthetic Sequence

<400> SEQUENCE: 263
ctacagtggc cttatccc                                                      18

<210> SEQ ID NO 264
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 264
tacagtggcc ttatccc                                                       17

<210> SEQ ID NO 265
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 265
tcagtggcct tatccc                                                        16

<210> SEQ ID NO 266
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 266
cagtggcctt atccc                                                         15

<210> SEQ ID NO 267
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 267
gcctttctac agtggcctta tccct                                              25

<210> SEQ ID NO 268
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 268
cctttctaca gtggccttat ccct                                               24

<210> SEQ ID NO 269
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 269
ctttctacag tggccttatc cct                                                23
```

```
<210> SEQ ID NO 270
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 270
tttctacagt ggccttatcc ct                                              22

<210> SEQ ID NO 271
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 271
ttctacagtg gccttatccc t                                               21

<210> SEQ ID NO 272
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 272
tctacagtgg ccttatccct                                                 20

<210> SEQ ID NO 273
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 273
ctacagtggc cttatccct                                                  19

<210> SEQ ID NO 274
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 274
tacagtggcc ttatccct                                                   18

<210> SEQ ID NO 275
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 275
acagtggcct tatccct                                                    17

<210> SEQ ID NO 276
<211> LENGTH: 16
<212> TYPE: DNA
<213> ORGANISM: Artificial Sequence
<220> FEATURE:
<223> OTHER INFORMATION: Synthetic Sequence
```

-continued

```
<400> SEQUENCE: 276
cagtggcctt atccct                                                    16

<210> SEQ ID NO 277
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 277
agtggcctta tccct                                                     15

<210> SEQ ID NO 278
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 278
ggccuuggua uguuccugcu ucaug                                          25

<210> SEQ ID NO 279
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 279
gccuugguau guuccugcuu caug                                           24

<210> SEQ ID NO 280
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 280
ccuugguaug uuccugcuuc aug                                            23

<210> SEQ ID NO 281
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 281
cuugguaugu uccugcuuca ug                                             22

<210> SEQ ID NO 282
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 282
uugguauguu ccugcuucau g                                              21

<210> SEQ ID NO 283
```

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 283
ugguauguuc cugcuucaug                                                   20

<210> SEQ ID NO 284
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 284
gguauguucc ugcuucaug                                                    19

<210> SEQ ID NO 285
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 285
guauguuccu gcuucaug                                                     18

<210> SEQ ID NO 286
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 286
uauguuccug cuucaug                                                      17

<210> SEQ ID NO 287
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 287
auguuccugc uucaug                                                       16

<210> SEQ ID NO 288
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 288
uguuccugcu ucaug                                                        15

<210> SEQ ID NO 289
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 289
```
gccuugguau guuccugcuu caugc 25

<210> SEQ ID NO 290
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 290
ccuugguaug uuccugcuuc augc 24

<210> SEQ ID NO 291
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 291
cuugguaugu uccugcuuca ugc 23

<210> SEQ ID NO 292
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 292
uugguauguu ccugcuucau gc 22

<210> SEQ ID NO 293
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 293
ugguauguuc cugcuucaug c 21

<210> SEQ ID NO 294
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 294
gguauguucc ugcuucaugc 20

<210> SEQ ID NO 295
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 295
guauguuccu gcuucaugc 19

<210> SEQ ID NO 296
<211> LENGTH: 18
<212> TYPE: RNA

```
<213> ORGANISM: Artificial Sequence
<220> FEATURE:
<223> OTHER INFORMATION: Synthetic Sequence

<400> SEQUENCE: 296
uauguuccug cuucaugc                                                       18

<210> SEQ ID NO 297
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 297
auguuccugc uucaugc                                                        17

<210> SEQ ID NO 298
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 298
uguuccugcu ucaugc                                                         16

<210> SEQ ID NO 299
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 299
guuccugcuu caugc                                                          15

<210> SEQ ID NO 300
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 300
ccuugguaug uuccugcuuc augcc                                               25

<210> SEQ ID NO 301
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 301
cuugguaugu uccgcuuca ugcc                                                 24

<210> SEQ ID NO 302
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 302
uugguauguu ccugcuucau gcc                                                 23
```

```
<210> SEQ ID NO 303
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 303
ugguauguuc cugcuucaug cc                                              22

<210> SEQ ID NO 304
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 304
gguauguucc ugcuucaugc c                                               21

<210> SEQ ID NO 305
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 305
guauguuccu gcuucaugcc                                                 20

<210> SEQ ID NO 306
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 306
uauguuccug cuucaugcc                                                  19

<210> SEQ ID NO 307
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 307 auguccugc uucaugcc                                                    18

<210> SEQ ID NO 308
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 308 uguccugcu ucaugcc                                                     17

<210> SEQ ID NO 309
<211> LENGTH: 16
<212> TYPE: RNA
<213> ORGANISM: Artificial Sequence
<220> FEATURE:
```

<223> OTHER INFORMATION: Synthetic Sequence

<400> SEQUENCE: 309
guuccugcuu caugcc                                                         16

<210> SEQ ID NO 310
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 310
uuccugcuuc augcc                                                          15

<210> SEQ ID NO 311
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 311
cuugguaugu uccugcuuca ugccu                                               25

<210> SEQ ID NO 312
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 312
uugguauguu ccugcuucau gccu                                                24

<210> SEQ ID NO 313
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 313
ugguauguuc cugcuucaug ccu                                                 23

<210> SEQ ID NO 314
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 314
gguauguucc ugcuucaugc cu                                                  22

<210> SEQ ID NO 315
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 315
guauguuccu gcuucaugcc u                                                   21

```
<210> SEQ ID NO 316
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 316 uauguccug cuucaugccu                                               20

<210> SEQ ID NO 317
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 317 auguccugc uucaugccu                                                19

<210> SEQ ID NO 318
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 318 uguccugcu ucaugccu                                                 18

<210> SEQ ID NO 319
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 319 guccugcuu caugccu                                                  17

<210> SEQ ID NO 320
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 320 uccugcuuc augccu                                                   16

<210> SEQ ID NO 321
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 321
uccugcuuca ugccu                                                   15

<210> SEQ ID NO 322
<211> LENGTH: 25
<212> TYPE: RNA
<213> ORGANISM: Artificial Sequence
<220> FEATURE:
<223> OTHER INFORMATION: Synthetic Sequence
```

```
<400> SEQUENCE: 322
uugguauguu ccugcuucau gccuu                                         25

<210> SEQ ID NO 323
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 323
ugguauguuc cugcuucaug ccuu                                          24

<210> SEQ ID NO 324
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 324
gguauguucc ugcuucaugc cuu                                           23

<210> SEQ ID NO 325
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 325
guauguuccu gcuucaugcc uu                                            22

<210> SEQ ID NO 326
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 326 uauguccug cuucaugccu u                                              21

<210> SEQ ID NO 327
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 327 auguccugc uucaugccuu                                                20

<210> SEQ ID NO 328
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 328 uguccugcu ucaugccuu                                                 19

<210> SEQ ID NO 329
<211> LENGTH: 18
```

```
<212> TYPE: RNA
<213> ORGANISM: Artificial Sequence
<220> FEATURE:
<223> OTHER INFORMATION: Synthetic Sequence

<400> SEQUENCE: 329
guuccugcuu caugccuu                                                      18

<210> SEQ ID NO 330
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 330
uuccugcuuc augccuu                                                       17

<210> SEQ ID NO 331
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 331
uccugcuuca ugccuu                                                        16

<210> SEQ ID NO 332
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 332
ccugcuucau gccuu                                                         15

<210> SEQ ID NO 333
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 333
ugguauguuc cugcuucaug ccuuu                                              25

<210> SEQ ID NO 334
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 334
gguauguucc ugcuucaugc cuuu                                               24

<210> SEQ ID NO 335
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 335
```
guauguuccu gcuucaugcc uuu        23

<210> SEQ ID NO 336
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 336
uauguuccug cuucaugccu uu        22

<210> SEQ ID NO 337
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 337 auguccugc uucaugccuu u        21

<210> SEQ ID NO 338
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 338 uguccugcu ucaugccuuu        20

<210> SEQ ID NO 339
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 339 guccugcuu caugccuuu        19

<210> SEQ ID NO 340
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 340
uuccugcuuc augccuuu        18

<210> SEQ ID NO 341
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 341
uccugcuuca ugccuuu        17

<210> SEQ ID NO 342
<211> LENGTH: 16
<212> TYPE: RNA
<213> ORGANISM: Artificial Sequence -continued
<220> FEATURE:
<223> OTHER INFORMATION: Synthetic Sequence

<400> SEQUENCE: 342
ccugcuucau gccuuu                                                     16

<210> SEQ ID NO 343
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 343
cugcuucaug ccuuu                                                      15

<210> SEQ ID NO 344
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 344
gguauguucc ugcuucaugc cuuuc                                           25

<210> SEQ ID NO 345
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 345
guauguuccu gcuucaugcc uuuc                                            24

<210> SEQ ID NO 346
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 346
uauguuccug cuucaugccu uuc                                             23

<210> SEQ ID NO 347
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 347 auguccugc uucaugccuu uc                                               22

<210> SEQ ID NO 348
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 348 uguccugcu ucaugccuuu c                                                21

```
<210> SEQ ID NO 349
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 349
guuccugcuu caugccuuuc                                              20

<210> SEQ ID NO 350
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 350
uuccugcuuc augccuuuc                                               19

<210> SEQ ID NO 351
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 351
uccugcuuca ugccuuuc                                                18

<210> SEQ ID NO 352
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 352
ccugcuucau gccuuuc                                                 17

<210> SEQ ID NO 353
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 353
cugcuucaug ccuuuc                                                  16

<210> SEQ ID NO 354
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 354
ugcuucaugc cuuuc                                                   15

<210> SEQ ID NO 355
<211> LENGTH: 25
<212> TYPE: RNA
<213> ORGANISM: Artificial Sequence
<220> FEATURE:
<223> OTHER INFORMATION: Synthetic Sequence
```

```
<400> SEQUENCE: 355
guauguuccu gcuucaugcc uuucu                                          25

<210> SEQ ID NO 356
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 356
uauguuccug cuucaugccu uucu                                           24

<210> SEQ ID NO 357
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 357
auguuccugc uucaugccuu ucu                                            23

<210> SEQ ID NO 358
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 358
uguuccugcu ucaugccuuu cu                                             22

<210> SEQ ID NO 359
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 359
guuccugcuu caugccuuuc u                                              21

<210> SEQ ID NO 360
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 360
uuccugcuuc augccuuucu                                                20

<210> SEQ ID NO 361
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 361
uccugcuuca ugccuuucu                                                 19

<210> SEQ ID NO 362
```

```
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 362
ccugcuucau gccuuucu                                                        18

<210> SEQ ID NO 363
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 363
cugcuucaug ccuuucu                                                         17

<210> SEQ ID NO 364
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 364
ugcuucaugc cuuucu                                                          16

<210> SEQ ID NO 365
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 365
gcuucaugcc uuucu                                                           15

<210> SEQ ID NO 366
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 366
uauguuccug cuucaugccu uucua                                                25

<210> SEQ ID NO 367
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 367
auguuccugc uucaugccuu ucua                                                 24

<210> SEQ ID NO 368
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 368
```
uguuccugcu ucaugccuuu cua                                          23

<210> SEQ ID NO 369
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 369
guuccugcuu caugccuuuc ua                                           22

<210> SEQ ID NO 370
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 370
uuccugcuuc augccuuucu a                                            21

<210> SEQ ID NO 371
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 371
uccugcuuca ugccuuucua                                              20

<210> SEQ ID NO 372
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 372
ccugcuucau gccuuucua                                               19

<210> SEQ ID NO 373
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 373
cugcuucaug ccuuucua                                                18

<210> SEQ ID NO 374
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 374
ugcuucaugc cuuucua                                                 17

<210> SEQ ID NO 375
<211> LENGTH: 16
<212> TYPE: RNA

```
<213> ORGANISM: Artificial Sequence
<220> FEATURE:
<223> OTHER INFORMATION: Synthetic Sequence

<400> SEQUENCE: 375
gcuucaugcc uuucua                                                      16

<210> SEQ ID NO 376
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 376
cuucaugccu uucua                                                       15

<210> SEQ ID NO 377
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 377
auguuccugc uucaugccuu ucuac                                            25

<210> SEQ ID NO 378
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 378
uguuccugcu ucaugccuuu cuac                                             24

<210> SEQ ID NO 379
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 379
guuccugcuu caugccuuuc uac                                              23

<210> SEQ ID NO 380
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 380
uuccugcuuc augccuuucu ac                                               22

<210> SEQ ID NO 381
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 381
uccugcuuca ugccuuucua c                                                21
```

```
<210> SEQ ID NO 382
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 382
ccugcuucau gccuuucuac                                                    20

<210> SEQ ID NO 383
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 383
cugcuucaug ccuuucuac                                                     19

<210> SEQ ID NO 384
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 384
ugcuucaugc cuuucuac                                                      18

<210> SEQ ID NO 385
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 385
gcuucaugcc uuucuac                                                       17

<210> SEQ ID NO 386
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 386
cuucaugccu uucuac                                                        16

<210> SEQ ID NO 387
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 387
uucaugccuu ucuac                                                         15

<210> SEQ ID NO 388
<211> LENGTH: 25
<212> TYPE: RNA
<213> ORGANISM: Artificial Sequence
<220> FEATURE:
```

<223> OTHER INFORMATION: Synthetic Sequence

<400> SEQUENCE: 388 uguccugcu ucaugccuuu cuaca                                      25

<210> SEQ ID NO 389
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 389 guccugcuu caugccuuuc uaca                                       24

<210> SEQ ID NO 390
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 390
uuccugcuuc augccuuucu aca                                       23

<210> SEQ ID NO 391
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 391
uccugcuuca ugccuuucua ca                                        22

<210> SEQ ID NO 392
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 392
ccugcuucau gccuuucuac a                                         21

<210> SEQ ID NO 393
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 393
cugcuucaug ccuuucuaca                                           20

<210> SEQ ID NO 394
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 394
ugcuucaugc cuuucuaca                                            19

```
<210> SEQ ID NO 395
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 395
gcuucaugcc uuucuaca                                                 18

<210> SEQ ID NO 396
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 396
cuucaugccu uucuaca                                                  17

<210> SEQ ID NO 397
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 397
uucaugccuu ucuaca                                                   16

<210> SEQ ID NO 398
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 398
ucaugccuuu cuaca                                                    15

<210> SEQ ID NO 399
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 399
guuccugcuu caugccuuuc uacag                                         25

<210> SEQ ID NO 400
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 400
uuccugcuuc augccuuucu acag                                          24

<210> SEQ ID NO 401
<211> LENGTH: 23
<212> TYPE: RNA
<213> ORGANISM: Artificial Sequence
<220> FEATURE:
<223> OTHER INFORMATION: Synthetic Sequence
```

<400> SEQUENCE: 401
uccugcuuca ugccuuucua cag                                   23

<210> SEQ ID NO 402
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 402
ccugcuucau gccuuucuac ag                                    22

<210> SEQ ID NO 403
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 403
cugcuucaug ccuuucuaca g                                     21

<210> SEQ ID NO 404
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 404
ugcuucaugc cuuucuacag                                       20

<210> SEQ ID NO 405
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 405
gcuucaugcc uuucuacag                                        19

<210> SEQ ID NO 406
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 406
cuucaugccu uucuacag                                         18

<210> SEQ ID NO 407
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 407
uucaugccuu ucuacag                                          17

<210> SEQ ID NO 408
<211> LENGTH: 16

```
<212> TYPE: RNA
<213> ORGANISM: Artificial Sequence
<220> FEATURE:
<223> OTHER INFORMATION: Synthetic Sequence

<400> SEQUENCE: 408
ucaugccuuu cuacag                                                          16

<210> SEQ ID NO 409
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 409
caugccuuuc uacag                                                           15

<210> SEQ ID NO 410
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 410
uuccugcuuc augccuuucu acagu                                                25

<210> SEQ ID NO 411
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 411
uccugcuuca ugccuuucua cagu                                                 24

<210> SEQ ID NO 412
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 412
ccugcuucau gccuuucuac agu                                                  23

<210> SEQ ID NO 413
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 413
cugcuucaug ccuuucuaca gu                                                   22

<210> SEQ ID NO 414
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 414
```
ugcuucaugc cuuucuacag u                                           21

<210> SEQ ID NO 415
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 415
gcuucaugcc uuucuacagu                                             20

<210> SEQ ID NO 416
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 416
cuucaugccu uucuacagu                                              19

<210> SEQ ID NO 417
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 417
uucaugccuu ucuacagu                                               18

<210> SEQ ID NO 418
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 418
ucaugccuuu cuacagu                                                17

<210> SEQ ID NO 419
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 419
caugccuuuc uacagu                                                 16

<210> SEQ ID NO 420
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 420
augccuuucu acagu                                                  15

<210> SEQ ID NO 421
<211> LENGTH: 25
<212> TYPE: RNA
<213> ORGANISM: Artificial Sequence -continued

```
<220> FEATURE:
<223> OTHER INFORMATION: Synthetic Sequence

<400> SEQUENCE: 421
uccugcuuca ugccuuucua cagug                                           25

<210> SEQ ID NO 422
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 422
ccugcuucau gccuuucuac agug                                            24

<210> SEQ ID NO 423
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 423
cugcuucaug ccuuucuaca gug                                             23

<210> SEQ ID NO 424
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 424
ugcuucaugc cuuucuacag ug                                              22

<210> SEQ ID NO 425
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 425
gcuucaugcc uuucuacagu g                                               21

<210> SEQ ID NO 426
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 426
cuucaugccu uucuacagug                                                 20

<210> SEQ ID NO 427
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 427
uucaugccuu ucuacagug                                                  19
```

<210> SEQ ID NO 428
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 428
ucaugccuuu cuacagug                                                    18

<210> SEQ ID NO 429
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 429
caugccuuuc uacagug                                                     17

<210> SEQ ID NO 430
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 430
augccuuucu acagug                                                      16

<210> SEQ ID NO 431
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 431
ugccuuucua cagug                                                       15

<210> SEQ ID NO 432
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 432
ccugcuucau gccuuucuac agugg                                            25

<210> SEQ ID NO 433
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 433
cugcuucaug ccuuucuaca gugg                                             24

<210> SEQ ID NO 434
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 434
ugcuucaugc cuuucuacag ugg                                           23

<210> SEQ ID NO 435
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 435
gcuucaugcc uuucuacagu gg                                            22

<210> SEQ ID NO 436
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 436
cuucaugccu uucuacagug g                                             21

<210> SEQ ID NO 437
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 437
uucaugccuu ucuacagugg                                               20

<210> SEQ ID NO 438
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 438
ucaugccuuu cuacagugg                                                19

<210> SEQ ID NO 439
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 439
caugccuuuc uacagugg                                                 18

<210> SEQ ID NO 440
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 440
augccuuucu acagugg                                                  17

<210> SEQ ID NO 441

-continued

<210> SEQ ID NO 441
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 441
ugccuuucua cagugg                                                         16

<210> SEQ ID NO 442
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 442
gccuuucuac agugg                                                          15

<210> SEQ ID NO 443
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 443
cugcuucaug ccuuucuaca guggc                                               25

<210> SEQ ID NO 444
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 444
ugcuucaugc cuuucuacag uggc                                                24

<210> SEQ ID NO 445
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 445
gcuucaugcc uuucuacagu ggc                                                 23

<210> SEQ ID NO 446
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 446
cuucaugccu uucuacagug gc                                                  22

<210> SEQ ID NO 447
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 447

-continued uucaugccuu ucuacagugg c   21

<210> SEQ ID NO 448
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 448
ucaugccuuu cuacaguggc   20

<210> SEQ ID NO 449
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 449
caugccuuuc uacaguggc   19

<210> SEQ ID NO 450
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 450
augccuuucu acaguggc   18

<210> SEQ ID NO 451
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 451
ugccuuucua caguggc   17

<210> SEQ ID NO 452
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 452
gccuuucuac aguggc   16

<210> SEQ ID NO 453
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 453
ccuuucuaca guggc   15

<210> SEQ ID NO 454
<211> LENGTH: 25
<212> TYPE: RNA

<213> ORGANISM: Artificial Sequence
<220> FEATURE:
<223> OTHER INFORMATION: Synthetic Sequence

<400> SEQUENCE: 454
ugcuucaugc cuuucuacag uggcc                                       25

<210> SEQ ID NO 455
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 455
gcuucaugcc uuucuacagu ggcc                                        24

<210> SEQ ID NO 456
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 456
cuucaugccu uucuacagug gcc                                         23

<210> SEQ ID NO 457
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 457
uucaugccuu ucuacagugg cc                                          22

<210> SEQ ID NO 458
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 458
ucaugccuuu cuacaguggc c                                           21

<210> SEQ ID NO 459
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 459
caugccuuuc uacaguggcc                                             20

<210> SEQ ID NO 460
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 460
augccuuucu acaguggcc                                              19

<210> SEQ ID NO 461
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 461
ugccuuucua caguggcc                                                 18

<210> SEQ ID NO 462
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 462
gccuuucuac aguggcc                                                  17

<210> SEQ ID NO 463
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 463
ccuuucuaca guggcc                                                   16

<210> SEQ ID NO 464
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 464
cuuucuacag uggcc                                                    15

<210> SEQ ID NO 465
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 465
gcuucaugcc uuucuacagu ggccu                                         25

<210> SEQ ID NO 466
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 466
cuucaugccu uucuacagug gccu                                          24

<210> SEQ ID NO 467
<211> LENGTH: 23
<212> TYPE: RNA
<213> ORGANISM: Artificial Sequence
<220> FEATURE:

-continued

<223> OTHER INFORMATION: Synthetic Sequence

<400> SEQUENCE: 467
uucaugccuu ucuacagugg ccu                                          23

<210> SEQ ID NO 468
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 468
ucaugccuuu cuacaguggc cu                                           22

<210> SEQ ID NO 469
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 469
caugccuuuc uacagguggcc u                                           21

<210> SEQ ID NO 470
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 470
augccuuucu acagguggccu                                             20

<210> SEQ ID NO 471
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 471
ugccuuucua cagguggccu                                              19

<210> SEQ ID NO 472
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 472
gccuuucuac agguggccu                                               18

<210> SEQ ID NO 473
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 473
ccuuucuaca gguggccu                                                17

```
<210> SEQ ID NO 474
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 474
cuuucuacag uggccu                                                    16

<210> SEQ ID NO 475
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 475
uuucuacagu ggccu                                                     15

<210> SEQ ID NO 476
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 476
cuucaugccu uucuacagug gccuu                                          25

<210> SEQ ID NO 477
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 477
uucaugccuu ucuacagugg ccuu                                           24

<210> SEQ ID NO 478
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 478
ucaugccuuu cuacaguggc cuu                                            23

<210> SEQ ID NO 479
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 479
caugccuuuc uacaguggcc uu                                             22

<210> SEQ ID NO 480
<211> LENGTH: 21
<212> TYPE: RNA
<213> ORGANISM: Artificial Sequence
<220> FEATURE:
<223> OTHER INFORMATION: Synthetic Sequence
```

```
<400> SEQUENCE: 480
augccuuucu acaguggccu u                                              21

<210> SEQ ID NO 481
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 481
ugccuuucua caguggccuu                                                20

<210> SEQ ID NO 482
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 482
gccuuucuac aguggccuu                                                 19

<210> SEQ ID NO 483
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 483
ccuuucuaca guggccuu                                                  18

<210> SEQ ID NO 484
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 484
cuuucuacag uggccuu                                                   17

<210> SEQ ID NO 485
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 485
uuucuacagu ggccuu                                                    16

<210> SEQ ID NO 486
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 486
uucuacagug gccuu                                                     15

<210> SEQ ID NO 487
<211> LENGTH: 25
```

```
<212> TYPE: RNA
<213> ORGANISM: Artificial Sequence
<220> FEATURE:
<223> OTHER INFORMATION: Synthetic Sequence

<400> SEQUENCE: 487
uucaugccuu ucuacagugg ccuua                                          25

<210> SEQ ID NO 488
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 488
ucaugccuuu cuacaguggc cuua                                           24

<210> SEQ ID NO 489
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 489
caugccuuuc uacaguggcc uua                                            23

<210> SEQ ID NO 490
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 490
augccuuucu acaguggccu ua                                             22

<210> SEQ ID NO 491
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 491
ugccuuucua caguggccuu a                                              21

<210> SEQ ID NO 492
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 492
gccuuucuac aguggccuua                                                20

<210> SEQ ID NO 493
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 493
```

```
ccuucuaca guggccuua                                              19

<210> SEQ ID NO 494
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 494
cuuucuacag uggccuua                                              18

<210> SEQ ID NO 495
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 495
uuucuacagu ggccuua                                               17

<210> SEQ ID NO 496
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 496
uucuacagug gccuua                                                16

<210> SEQ ID NO 497
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 497
ucuacagugg ccuua                                                 15

<210> SEQ ID NO 498
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 498
ucaugccuuu cuacaguggc cuuau                                      25

<210> SEQ ID NO 499
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 499
caugccuuuc uacaguggcc uuau                                       24

<210> SEQ ID NO 500
<211> LENGTH: 23
<212> TYPE: RNA
<213> ORGANISM: Artificial Sequence
```

```
<220> FEATURE:
<223> OTHER INFORMATION: Synthetic Sequence

<400> SEQUENCE: 500
augccuuucu acaguggccu uau                                               23

<210> SEQ ID NO 501
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 501
ugccuuucua caguggccuu au                                                22

<210> SEQ ID NO 502
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 502
gccuuucuac aguggccuua u                                                 21

<210> SEQ ID NO 503
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 503
ccuuucuaca guggccuuau                                                   20

<210> SEQ ID NO 504
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 504
cuuucuacag uggccuuau                                                    19

<210> SEQ ID NO 505
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 505
uuucuacagu ggccuuau                                                     18

<210> SEQ ID NO 506
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 506
uucuacagug gccuuau                                                      17
```

<210> SEQ ID NO 507
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 507
ucuacagugg ccuuau                                                         16

<210> SEQ ID NO 508
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 508
cuacaguggc cuuau                                                          15

<210> SEQ ID NO 509
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 509
caugccuuuc uacaguggcc uuauc                                               25

<210> SEQ ID NO 510
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 510
augccuuucu acaguggccu uauc                                                24

<210> SEQ ID NO 511
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 511
ugccuuucua caguggccuu auc                                                 23

<210> SEQ ID NO 512
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 512
gccuuucuac aguggccuua uc                                                  22

<210> SEQ ID NO 513
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 513 ccuucuaca guggccuuau c                                              21

<210> SEQ ID NO 514
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 514
cuuucuacag uggccuuauc                                               20

<210> SEQ ID NO 515
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 515
uuucuacagu ggccuuauc                                                19

<210> SEQ ID NO 516
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 516
uucuacagug gccuuauc                                                 18

<210> SEQ ID NO 517
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 517
ucuacagugg ccuuauc                                                  17

<210> SEQ ID NO 518
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 518
cuacaguggc cuuauc                                                   16

<210> SEQ ID NO 519
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 519
uacaguggcc uuauc                                                    15

<210> SEQ ID NO 520

```
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 520
augccuuucu acaguggccu uaucc                                              25

<210> SEQ ID NO 521
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 521
ugccuuucua caguggccuu aucc                                               24

<210> SEQ ID NO 522
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 522
gccuuucuac aguggccuua ucc                                                23

<210> SEQ ID NO 523
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 523
ccuuucuaca guggccuuau cc                                                 22

<210> SEQ ID NO 524
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 524
cuuucuacag uggccuuauc c                                                  21

<210> SEQ ID NO 525
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 525
uuucuacagu ggccuuaucc                                                    20

<210> SEQ ID NO 526
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 526
```
uucuacagug gccuuaucc                                                        19

<210> SEQ ID NO 527
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 527
ucuacagugg ccuuaucc                                                         18

<210> SEQ ID NO 528
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 528
cuacaguggc cuuaucc                                                          17

<210> SEQ ID NO 529
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 529
uacaguggcc uuaucc                                                           16

<210> SEQ ID NO 530
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 530
acaguggccu uaucc                                                            15

<210> SEQ ID NO 531
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 531
ugccuuucua caguggccuu auccc                                                 25

<210> SEQ ID NO 532
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 532
gccuuucuac aguggccuua uccc                                                  24

<210> SEQ ID NO 533
<211> LENGTH: 23
<212> TYPE: RNA

```
<213> ORGANISM: Artificial Sequence
<220> FEATURE:
<223> OTHER INFORMATION: Synthetic Sequence

<400> SEQUENCE: 533 ccuucuaca guggccuuau ccc                                              23

<210> SEQ ID NO 534
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 534 cuucuacag uggccuuauc cc                                               22

<210> SEQ ID NO 535
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 535
uuucuacagu ggccuuaucc c                                               21

<210> SEQ ID NO 536
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 536
uucuacagug gccuuauccc                                                 20

<210> SEQ ID NO 537
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 537
ucuacagugg ccuuauccc                                                  19

<210> SEQ ID NO 538
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 538
cuacaguggc cuuauccc                                                   18

<210> SEQ ID NO 539
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 539
uacaguggcc uuauccc                                                    17
```

```
<210> SEQ ID NO 540
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 540 ucagugggccu uauccc                                                        16

<210> SEQ ID NO 541
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 541
caguggccuu auccc                                                          15

<210> SEQ ID NO 542
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 542
gccuuucuac aguggccuua ucccu                                               25

<210> SEQ ID NO 543
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 543
ccuuucuaca guggccuuau cccu                                                24

<210> SEQ ID NO 544
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 544
cuuucuacag uggccuuauc ccu                                                 23

<210> SEQ ID NO 545
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 545
uuucuacagu ggccuuaucc cu                                                  22

<210> SEQ ID NO 546
<211> LENGTH: 21
<212> TYPE: RNA
<213> ORGANISM: Artificial Sequence
<220> FEATURE:
```

<223> OTHER INFORMATION: Synthetic Sequence

<400> SEQUENCE: 546
uucuacagug gccuuauccc u                                                 21

<210> SEQ ID NO 547
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 547
ucuacagugg ccuuauccu                                                    20

<210> SEQ ID NO 548
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 548
cuacaguggc cuuaucccu                                                    19

<210> SEQ ID NO 549
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 549
uacaguggcc uuaucccu                                                     18

<210> SEQ ID NO 550
<211> LENGTH: 17
<212> TYPE: RNA
<213> ORGANISM: Artificial Sequence
<220> FEATURE:
<223> OTHER INFORMATION: Synthetic Sequence

<400> SEQUENCE: 550
acaguggccu uaucccu                                                      17

<210> SEQ ID NO 551
<211> LENGTH: 16
<212> TYPE: RNA
<213> ORGANISM: Artificial Sequence
<220> FEATURE:
<223> OTHER INFORMATION: Synthetic Sequence

<400> SEQUENCE: 551
caguggccuu aucccu                                                       16

<210> SEQ ID NO 552
<211> LENGTH: 15
<212> TYPE: RNA
<213> ORGANISM: Artificial Sequence
<220> FEATURE:
<223> OTHER INFORMATION: Synthetic Sequence

<400> SEQUENCE: 552 aguggccuuaucccu                                                         15

```
<210> SEQ ID NO 553
<211> LENGTH: 64
<212> TYPE: DNA
<213> ORGANISM: Homo sapiens

<400> SEQUENCE: 553
gccttggtat gttcctgctt catcccttc tacagtggcc ttatccctcc ttccttcaga      60
ggcg                                                                  64

<210> SEQ ID NO 554
<211> LENGTH: 64
<212> TYPE: DNA
<213> ORGANISM: Homo sapiens

<400> SEQUENCE: 554
gccttggtat gttcctgctt catgcctttc tacagtggcc ttatccctcc ttccttcaga     60
ggcg                                                                  64
```